(12) United States Patent
Cope et al.

(10) Patent No.: US 11,135,060 B2
(45) Date of Patent: Oct. 5, 2021

(54) TRANSSEPTAL DELIVERY SYSTEMS HAVING A DEFLECTING SEGMENT AND METHODS OF USE

(71) Applicant: Medtronic Vascular, Inc., Santa Rosa, CA (US)

(72) Inventors: Jonathan Cope, Santa Rosa, CA (US); Kieran Coughlan, Galway (IE); Faraz Ul Hassan, Mayo (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 251 days.

(21) Appl. No.: 16/109,861

(22) Filed: Aug. 23, 2018

(65) Prior Publication Data

US 2019/0060068 A1 Feb. 28, 2019

Related U.S. Application Data

(60) Provisional application No. 62/549,575, filed on Aug. 24, 2017.

(51) Int. Cl.
*A61F 2/24* (2006.01)
(52) U.S. Cl.
CPC .......... *A61F 2/2439* (2013.01); *A61F 2/2436* (2013.01); *A61F 2/2418* (2013.01); *A61F 2230/0091* (2013.01)
(58) Field of Classification Search
CPC ..... A61F 2/2439; A61F 2/2436; A61F 2/2418
See application file for complete search history.

(56) References Cited

U.S. PATENT DOCUMENTS

| | | | |
|---|---|---|---|
| 7,621,948 B2 | 11/2009 | Herrmann et al. |
| 8,105,375 B2 | 1/2012 | Navia et al. |
| 8,591,460 B2 | 11/2013 | Wilson et al. |
| 9,078,994 B2 | 7/2015 | Rosenman et al. |
| 2004/0260394 A1 | 12/2004 | Douk et al. |

(Continued)

FOREIGN PATENT DOCUMENTS

| | | |
|---|---|---|
| WO | 2009/091509 A1 | 7/2009 |
| WO | 2011/025945 A1 | 3/2011 |
| WO | 2014/121280 A2 | 8/2014 |

OTHER PUBLICATIONS

International Search Report, Application No. PCT/2018/047806, dated Dec. 8, 2018.

*Primary Examiner* — Tuan V Nguyen

(57) ABSTRACT

A delivery system for delivering a heart valve prosthesis includes a delivery catheter and a heart valve prosthesis. The delivery catheter includes an outer sheath, an inner shaft, a distal nosecone, and a deflecting segment. The inner shaft is slidably disposed within the outer sheath. A distal end of the inner shaft is coupled to a proximal end of the deflecting segment, and a distal end of the deflecting segment is coupled to the distal nosecone. The deflecting segment includes a delivery state with the deflecting segment and the distal nosecone having a combined first longitudinal length. The deflecting segment further includes a deflected state with the deflecting segment having a second longitudinal length that is less than the first longitudinal length. The heart valve prosthesis includes a radially collapsed configuration and a radially expanded configuration. The deflecting segment is shape-set to the deflected state.

14 Claims, 16 Drawing Sheets

(56) References Cited

U.S. PATENT DOCUMENTS

| | | | |
|---|---|---|---|
| 2007/0203560 A1* | 8/2007 | Forster | A61F 2/2433 |
| | | | 623/1.11 |
| 2010/0286768 A1* | 11/2010 | Alkhatib | A61F 2/2418 |
| | | | 623/2.11 |
| 2011/0208297 A1 | 8/2011 | Tuval et al. | |
| 2012/0041533 A1* | 2/2012 | Bertolino | A61B 1/0125 |
| | | | 623/1.11 |
| 2012/0059458 A1 | 3/2012 | Buchbinder et al. | |
| 2012/0239002 A1* | 9/2012 | Griswold | A61M 25/0074 |
| | | | 604/523 |
| 2013/0060328 A1 | 3/2013 | Rothstein | |
| 2013/0226290 A1 | 8/2013 | Yellin et al. | |
| 2013/0231735 A1 | 9/2013 | Deem et al. | |
| 2013/0310928 A1 | 11/2013 | Morriss et al. | |
| 2014/0039611 A1 | 2/2014 | Lane et al. | |
| 2014/0340669 A1 | 11/2014 | Gillespie et al. | |
| 2014/0379074 A1 | 12/2014 | Spence et al. | |
| 2015/0119981 A1 | 4/2015 | Khairkhahan et al. | |
| 2015/0297346 A1 | 4/2015 | Duffy et al. | |
| 2015/0238315 A1 | 8/2015 | Rabito et al. | |
| 2018/0206989 A1* | 7/2018 | O'Connell | A61F 2/2466 |

* cited by examiner

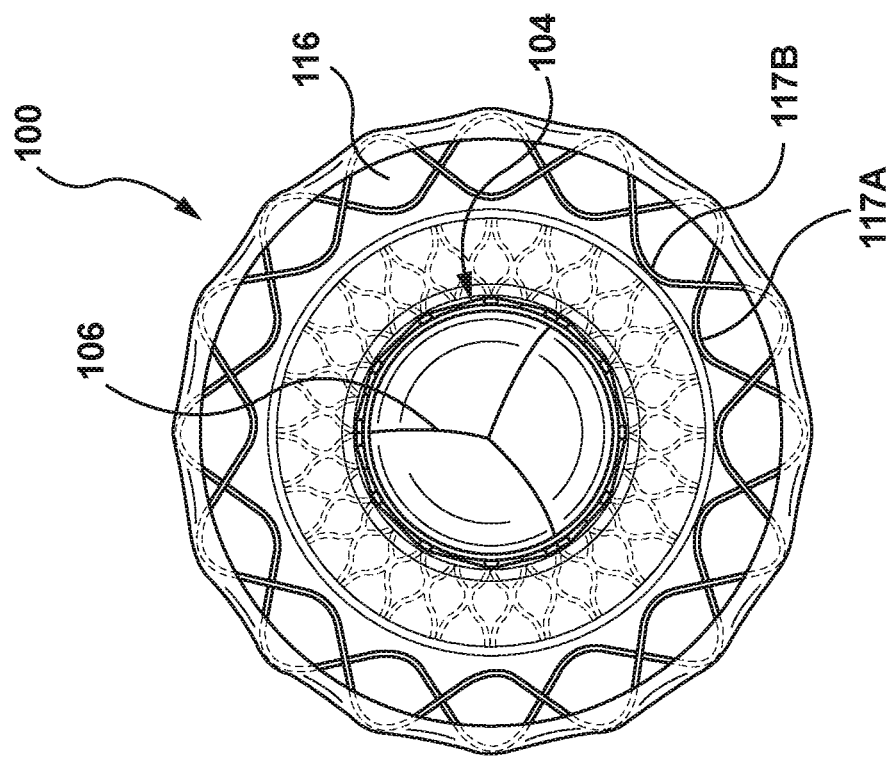
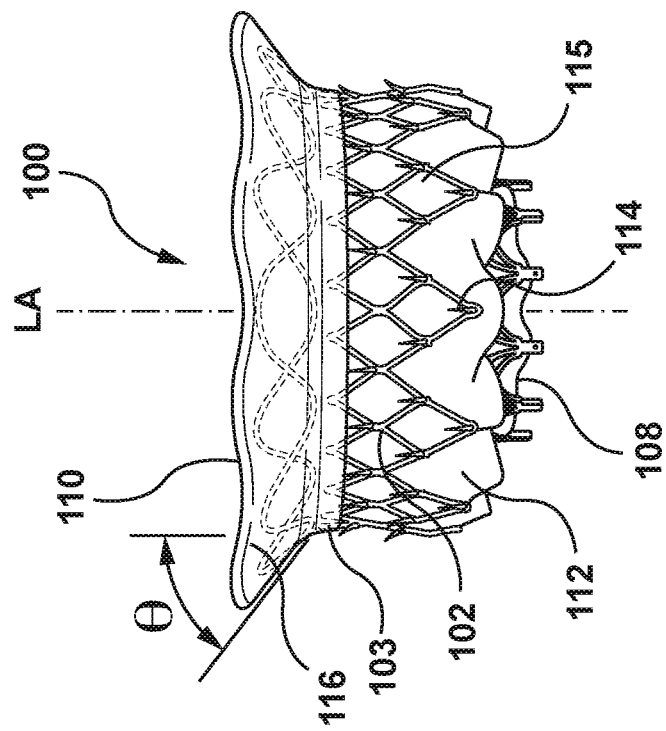
FIG. 3C
FIG. 3B

TRANSSEPTAL DELIVERY SYSTEMS HAVING A DEFLECTING SEGMENT AND METHODS OF USE

CROSS-REFERENCE TO RELATED APPLICATIONS

This application claims the benefit under 35 U.S.C. § 119(e) of U.S. Provisional Application No. 62/549,575 filed Aug. 24, 2017, the contents of which are incorporated by reference herein in their entirety.

FIELD OF THE INVENTION

The present invention relates to systems and methods of deploying a heart valve prosthesis at the site of a native heart valve. More particularly, the present invention relates to transseptal delivery systems with deflecting segments for delivering heart valve prostheses within native heart valves.

BACKGROUND OF THE INVENTION

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs to the remaining body. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream direction.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate. Valvular stenosis may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses can be delivered while in a low-profile or radially collapsed configuration so that the heart valve prosthesis can be advanced through the patient's vasculature. Once positioned at the treatment site, the heart valve prosthesis is expanded to engage tissue at the diseased heart valve region to, for instance, hold the heart valve prosthesis in position. For repair and replacement of a native mitral valve, it may be desirable in some circumstances for a clinician to utilize a transseptal approach to the native mitral valve with a catheter-based delivery system. However, challenges exist with maneuvering a catheter-based delivery system within the confined space of the left atrium that may limit a clinician's ability to properly position a heart valve prosthesis at the native mitral valve when using a transseptal approach. More specifically, as the heart valve prosthesis is deployed, a distal tip or nosecone of a delivery catheter may undesirably be advanced within the left ventricle making successful deployment of the heart valve prosthesis difficult and potentially may result in damage to the wall or myocardial tissue of the left ventricle during deployment.

Accordingly, there is a need for catheter-based delivery systems that may be advanced to a native mitral valve via a transseptal approach and that provide for a successful deployment of a replacement mitral valve while preventing damage to the left ventricle.

BRIEF SUMMARY OF THE INVENTION

Embodiments hereof relate to a delivery system for percutaneously delivering a heart valve prosthesis to a site of a native heart valve. The delivery system includes a delivery catheter and a heart valve prosthesis. The delivery catheter includes an outer sheath, an inner shaft, a distal nosecone, and a deflecting segment. The inner shaft is slidably disposed within the outer sheath. The distal nosecone is disposed at a distal portion of the delivery catheter. A proximal end of the deflecting segment is coupled to a distal end of the inner shaft, and a distal end of the deflecting segment is coupled to the distal nosecone. The deflecting segment includes a delivery state and a deflected state. When the deflecting segment is in the delivery state, the deflecting segment and the distal nosecone have a combined first longitudinal length along a central longitudinal axis of a distal portion of the inner shaft. When the deflecting segment is in the deflected state, the deflecting segment has a second longitudinal length along the central longitudinal axis of the distal portion of the inner shaft, wherein the first longitudinal length is greater than the second longitudinal length.

Embodiments hereof also relate to a delivery catheter for percutaneously delivering a heart valve prosthesis to a site of a native heart valve. The heart valve prosthesis is radially expandable from a radially collapsed configuration to a radially expanded configuration. The delivery catheter includes an outer sheath, an inner shaft, a distal nosecone, and a deflecting segment. The inner shaft is slidably disposed within the outer shaft. A proximal end of the distal nosecone is coupled to a distal end of the deflecting segment. A distal end of the deflecting segment is coupled to the distal nosecone. The deflecting segment includes a delivery state and a deflected state. When the deflecting segment is in the delivery state, the deflecting segment and the distal nosecone have a combined first longitudinal length along a central longitudinal axis of a distal portion of the inner shaft. When the deflecting segment is in the deflected state, the deflecting segment has a second longitudinal length along the central longitudinal axis of the distal portion of the inner shaft, wherein the combined first longitudinal length is greater than the second longitudinal length.

Embodiments hereof further relate to a method of delivering, positioning and deploying a heart valve prosthesis at a site of a native heart valve. A delivery catheter with a heart valve prosthesis in a radially collapsed configuration disposed therein is advanced to a native heart valve. The delivery catheter includes an outer sheath and an inner shaft assembly. The inner shaft assembly includes an inner shaft, a deflecting segment in a delivery state, and a distal nosecone. The heart valve prosthesis is positioned within an annulus of the native heart valve. The outer sheath is proximally retracted to release a first portion of the heart valve prosthesis. The delivery catheter is advanced to engage the first portion of the heart valve prosthesis with the tissue of the native heart valve. The inner shaft assembly is distally advanced to release a second portion of the heart valve prosthesis from the distal nosecone, and the deflecting segment transitions from the delivery state to a deflected state. The outer sheath of the delivery catheter is advanced through the heart valve prosthesis. The inner shaft assembly is proximally retracted and the deflecting segment transitions from the deflected state to the delivery state as it is received within a distal portion of the outer sheath.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3B is a side view illustration of the heart valve prosthesis of FIG. 3A, wherein the heart valve prosthesis is in the radially expanded configuration.

FIG. 3C is a top view illustration of the heart valve prosthesis of FIG. 3A, wherein the heart valve prosthesis is in the radially expanded configuration.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a catheter and/or other system components hereof are with respect to a position or direction relative to the treating clinician. Thus, "distal" and "distally" refer to positions distant from or in a direction away from the treating clinician, and the terms "proximal" and "proximally" refer to positions near or in a direction toward the treating clinician. The terms "distal" and "proximal", when used in the following description to refer to a native vessel, native valve, or a device to be implanted into a native vessel or native valve, such as a heart valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of embodiments hereof is in the context of delivery systems for delivering a heart valve prosthesis within a native mitral valve, the delivery system described herein can also be used in other valves of the body, non-limiting examples of which include delivering a heart valve prosthesis within a native tricuspid valve, a native aortic valve, or for delivering a heart valve prosthesis within a failed previously implanted heart valve prosthesis. Furthermore, there is no intention to be bound by any expressed or implied theory presented in the preceding technical field, background, brief summary or the following detailed description.

Figure 1:
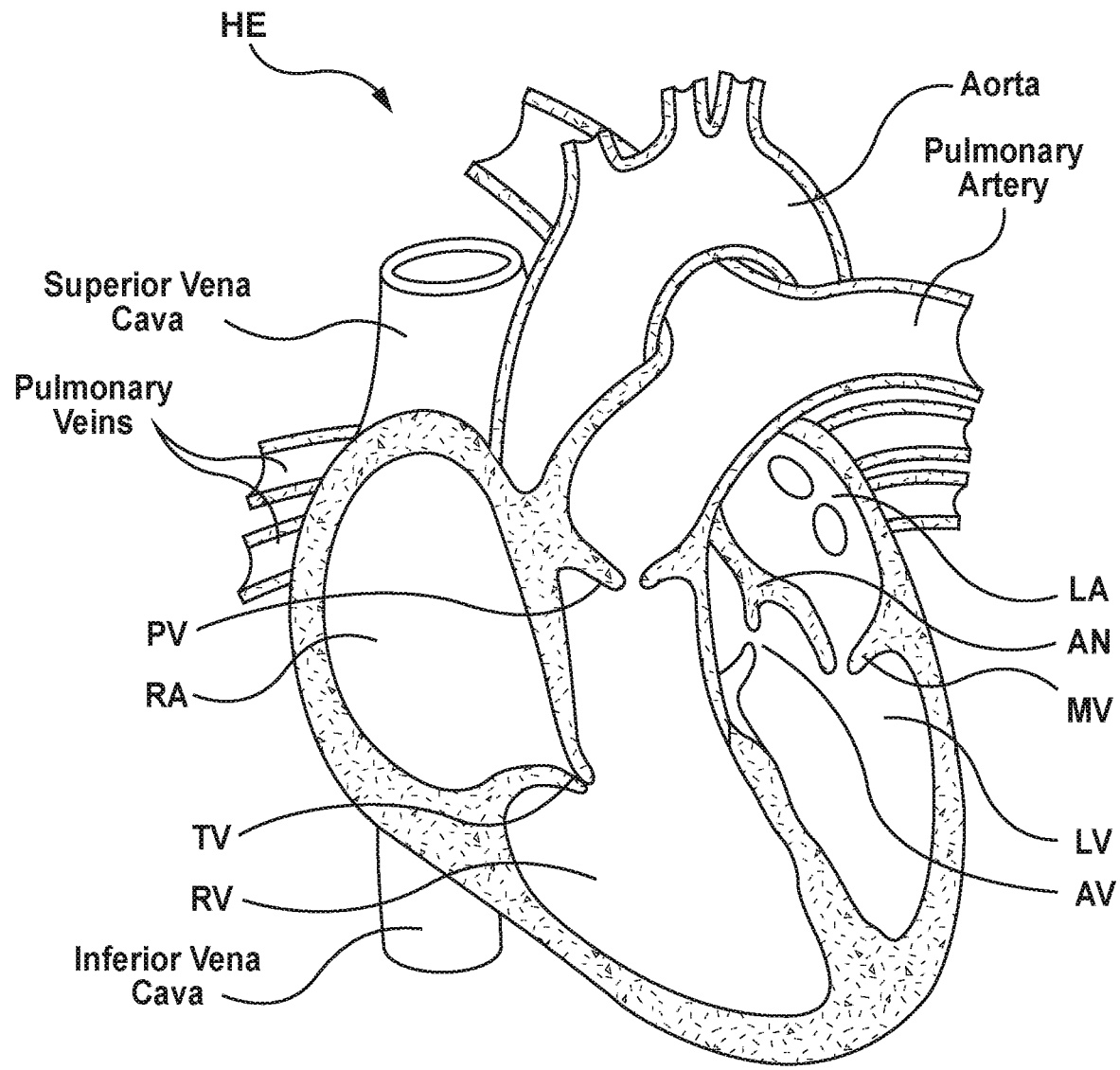
FIG. 1 is a schematic sectional illustration of a mammalian heart having native heart valve structures.
Figure 2A:
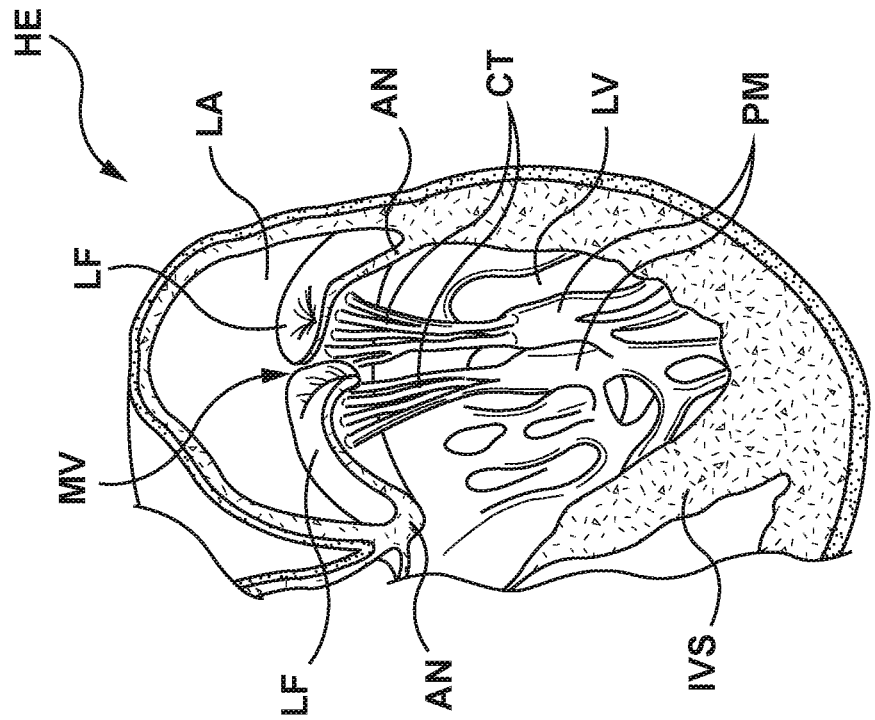
FIG. 2A is a schematic sectional illustration of a left ventricle of a mammalian heart showing anatomical structures and a native mitral valve.

FIG. 1 is a schematic sectional illustration of a mammalian heart HE that depicts the four heart chambers (right atrium RA, right ventricle RV, left atrium LA, left ventricle LV) and native valve structures (tricuspid valve TV, mitral valve MV, pulmonary valve PV, aortic valve AV). FIG. 2A is a schematic sectional illustration of a left ventricle LV of a mammalian heart HE showing anatomical structures and a native mitral valve MV. Referring to FIGS. 1 and 2A together, the heart HE comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

Figure 2B:
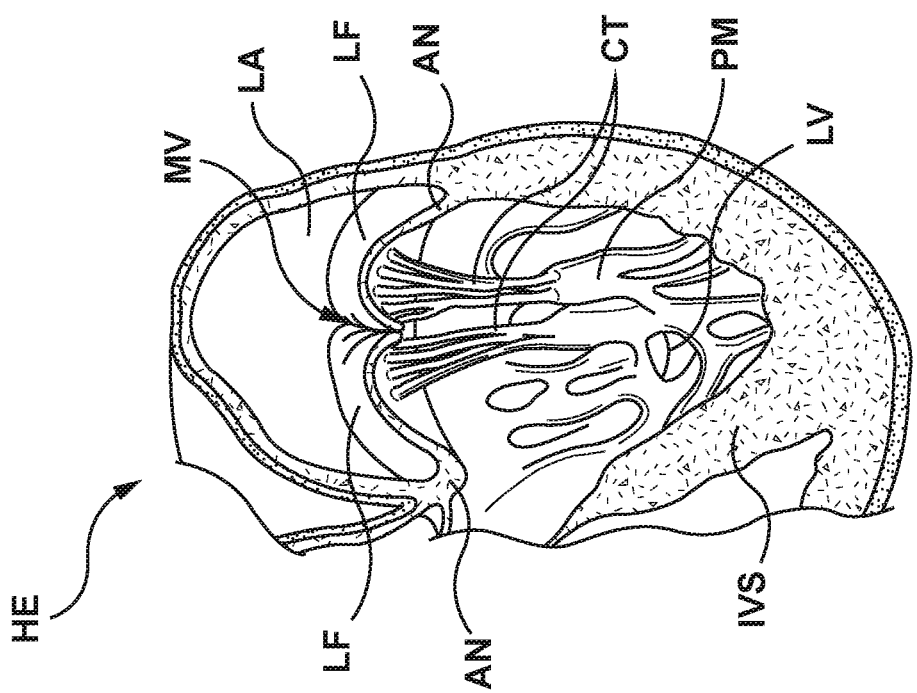
FIG. 2B is a schematic sectional illustration of the left ventricle of a heart having a prolapsed mitral valve in which the leaflets do not sufficiently coapt and which is suitable for replacement with a heart valve prosthesis via a delivery catheter in accordance with embodiments hereof.

In a healthy heart, as shown in FIG. 2A, the leaflets LF of the native mitral valve MV meet evenly at the free edges or "coapt" to close and prevent back flow of blood into the left atrium LA during contraction of the left ventricle LV. The tissue of the leaflets LF attach the surrounding heart structure via a dense fibrous ring of connective tissue called an annulus AN which is distinct from both the tissue of the leaflets LF as well as the adjoining muscular tissue of the heart wall. In general, the connective tissue at the annulus AN is more fibrous, tougher and stronger than leaflet tissue. The flexible tissue of the leaflets LF of the native mitral valve MV are connected to papillary muscles PM, which extend upwardly from the lower wall of the left ventricle LV and the interventricular septum IVS, via branching tendons called chordae tendinae CT. In a heart HE having a prolapsed mitral valve MV in which the leaflets LF do not sufficiently coapt or meet, as shown in FIG. 2B, leakage from the left ventricle LV into the left atrium LA will occur. Several structural defects can cause the mitral leaflets LF to prolapse, and subsequent regurgitation to occur, including ruptured chordae tendinae CT, impairment of papillary muscles PM (e.g., due to ischemic heart disease), and enlargement of the heart and/or mitral valve annulus AN (e.g., cardiomyopathy).

Figure 3A:
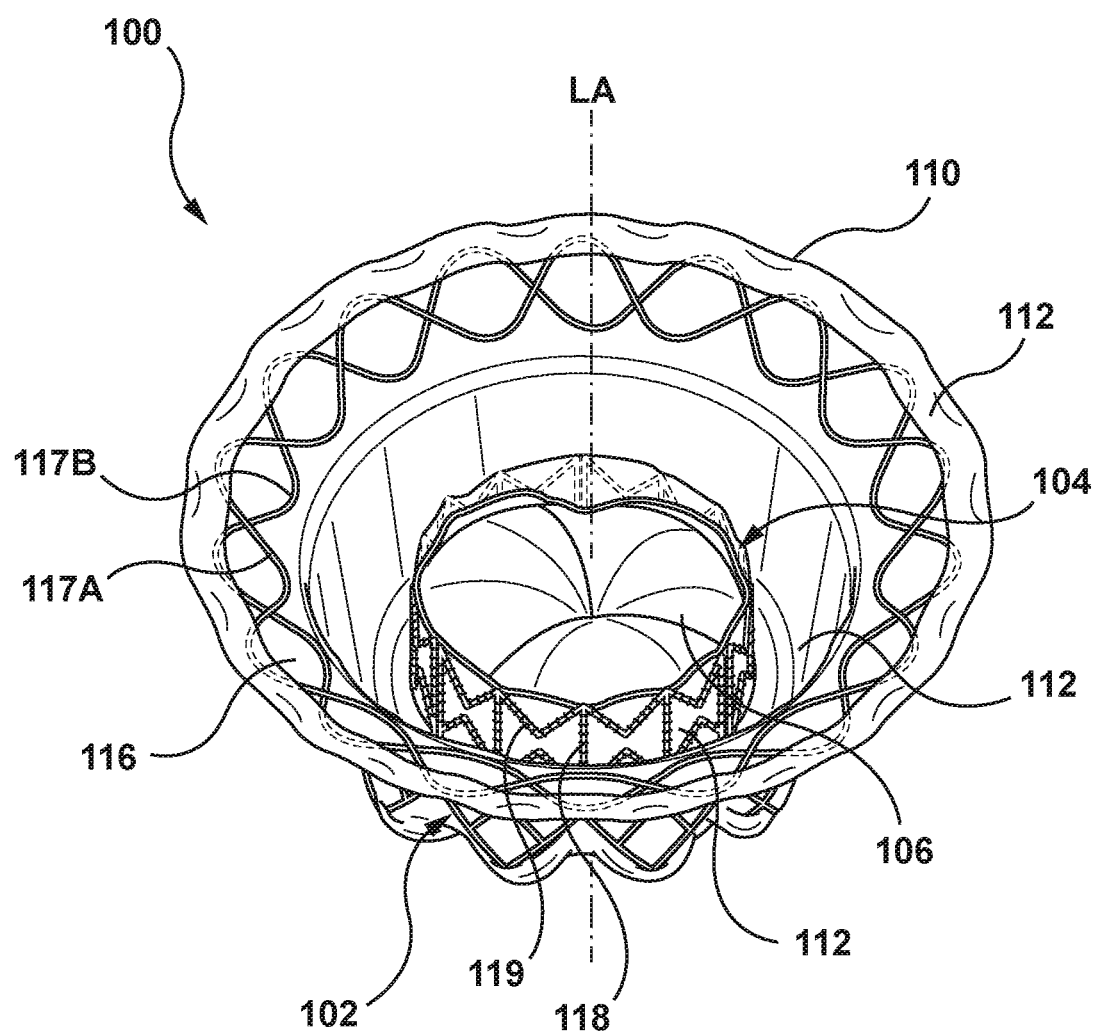
FIG. 3A is a perspective view illustration of an exemplary heart valve prosthesis for use in embodiments hereof, wherein the heart valve prosthesis is in a radially expanded configuration.

FIGS. 3A, 3B, 3C are perspective, side, and top views, respectively, of an exemplary heart valve prosthesis 100 for use in embodiments hereof, wherein the heart valve prosthesis 100 is in a radially expanded configuration. The heart valve prosthesis 100 is illustrated herein in order to facilitate description of delivery catheters and systems to be utilized in conjunction therewith according to embodiments hereof. It is understood that any number of alternate heart valve prostheses can be used with the methods and devices described herein. The heart valve prosthesis 100 is merely exemplary and is similar to heart valve prostheses described in more detail in U.S. Pat. No. 9,034,032 to McLean et al. and International Patent Application No. PCT/US2014/029549 to McLean et al, each of which is herein incorporated by reference in its entirety. Other non-limiting examples of transcatheter heart valve prostheses useful with systems and methods of the present disclosure are described in U.S. Patent Application Publication No. 2012/0101572 to Kovalsky et al., U.S. Patent Application Publication No. 2012/0035722 to Tuval, U.S. Patent Application Publication No. 2006/0265056 to Nguyen et al., U.S. Patent Application Publication No. 2007/05409266 to Birdsall, and U.S. Patent Application Publication No. 2007/05409269 to Dolan et al., each of which is incorporated by reference herein in its entirety.

As shown in FIGS. 3A-3C, the heart valve prosthesis 100 includes a flexible anchoring member 102 at least partially surrounding and coupled to an inner valve support 104. The heart valve prosthesis 100 further includes a prosthetic valve 106 coupled to, mounted within, or otherwise carried by the valve support 104. The heart valve prosthesis 100 is configured for placement within a native mitral valve and includes a downstream end or outflow portion 108 and an upstream end or inflow portion 110. The heart valve prosthesis 100 also includes one or more sealing members 112 and tissue engaging elements 114. For example, the tissue engaging elements 114 may be spikes or barbs disposed on an outer wall or surface of the anchoring member 102 and extend in an upward and/or radially outward direction to engage, and in some embodiments, penetrate the native tissue to facilitate retention or maintain position of the device in a desired implanted location. In another specific embodiment, the sealing members 112 may extend around an inner wall or surface of the anchoring member 102 and/or around an inner wall or surface of the valve support 104 to prevent paravalvular leaks between the heart valve prosthesis 100 and the native tissue and/or between the anchoring member 102 and the valve support 104.

The anchoring member 102 is a generally tubular stent or frame. In the embodiment shown in FIGS. 3A-3C, the anchoring member 102 has a funnel-like or hyperboloid shape or profile. Further, in the embodiment shown in FIGS. 3A-3C, the anchoring member 102 is a generally tubular stent with diamond-shaped openings 115 that may be formed by a laser-cut manufacturing method and/or another conventional stent forming methods. For example, the anchoring member 102 may be laser cut from a single metal tube into the desired geometry, creating a tubular scaffold of interconnected struts that form the diamond-shaped openings 115. The anchoring member 102 may then be shaped into a desired configuration, e.g. funnel-like or hyperboloid shape, using known shape-setting techniques for such materials. It will be understood the stent or frame of a heart valve prosthesis may have other shapes and configurations. In another embodiment, the anchoring member 102 may include a plurality of posts connected circumferentially by a plurality of struts as described herein with respect to the valve support 104.

The heart valve prosthesis 100 further includes a brim 116. The brim 116 is disposed at the inflow portion 110 of the heart valve prosthesis 100 and is attached to and extends from an inflow end 103 of the anchoring member 102. The brim 116 is a flared lip or ridge of the anchoring member 102 that extends at least partially radially outward relative to the anchoring member 102. As formed and as best shown in the side view of FIG. 3B, the brim 116 may be disposed at an angle θ relative to the outer wall or surface of the anchoring member 102. In the embodiment shown in FIGS. 3A-3C, the brim 116 includes two sinusoidal rings 117A, 117B and the sealing member 112 disposed over or covering at least on a downstream surface of the sinusoidal rings 117A, 117B. The sinusoidal rings 117A, 117B are disposed out of phase relative to each other, and may be woven together or may be disposed in an overlapping manner and coupled together.

The valve support 104 is also a generally cylindrical stent or frame that supports the prosthetic valve 106 within the interior of the valve support 104. In some embodiments, the valve support 104 includes a plurality of posts 118 connected circumferentially by a plurality of struts 119. The plurality of posts 118 and the plurality of struts 119 may be arranged in a variety of geometrical patterns that may expand and provide sufficient resilience and column strength for maintaining the integrity of prosthetic valve 106. For example, the plurality of posts 118 may extend longitudinally across multiple rows of the plurality of struts 119 to provide column strength to the valve support 104. Generally, the plurality of posts 118 may extend along an axial direction generally parallel to a longitudinal axis LA and the plurality of struts 119 may extend circumferentially around and transverse to the longitudinal axis LA. As will be understood, the stent or frame of a heart valve prosthesis may have other shapes and configurations. In another embodiment, the valve support 104 may be laser cut from a single metal tube into the desired geometry, creating a tubular scaffold of interconnected struts.

In embodiments hereof, both the anchoring member 102 and the valve support 104 are self-expanding to return to an expanded deployed state from a collapsed or constricted delivery state and may be made from materials such as, but not limited to stainless steel, a pseudo-elastic metal such as a nickel titanium alloy (e.g. NITINOL), or a so-called super alloy, which may have a base metal of nickel, cobalt, chromium, or other metal. "Self-expanding" as used herein means that a structure/component has a mechanical memory to return to the expanded or deployed configuration or state as described herein. Alternatively, the heart valve prosthesis 100 may be balloon-expandable. Whether the valve support 104 is self-expanding or balloon-expandable, the heart valve prosthesis 100 has a radially collapsed configuration for delivery within a delivery system and the radially expanded configuration for deployment within an annulus of a native heart valve.

As previously described, the heart valve prosthesis 100 includes the prosthetic valve 106 within the interior of the valve support 104. In an embodiment hereof, the prosthetic valve 106 is positioned adjacent to the inflow end of the valve support 104. The prosthetic valve 106 is configured as a one-way valve to allow blood flow in one direction and thereby regulate blood flow therethrough. The prosthetic valve 106 is capable of blocking flow in one direction to regulate flow therethrough via valve leaflets that may form a bicuspid or tricuspid replacement valve. More particularly, if the heart valve prosthesis 100 is configured for placement within a native heart valve having two leaflets such as the mitral valve, the prosthetic valve 106 includes two valve leaflets to form a bicuspid replacement valve that closes with pressure on the outflow and opens with pressure on the inflow. In other embodiments in accordance herewith, the prosthetic valve 106 may be a tricuspid replacement valve or may be a single leaflet replacement valve. The valve leaflets are sutured or otherwise securely and sealingly attached to an inner circumference of the valve support 104 and/or the sealing members 112 which encloses or lines the valve support 104.

The valve leaflets may be made of natural pericardial material obtained from, for example, heart valves, aortic roots, aortic walls, aortic leaflets, pericardial tissue, bypass grafts, blood vessels, intestinal submucosal tissue, umbilical tissue and the like from humans or animals, such as tissue from bovine, equine or porcine origins. Alternatively, the valve leaflets may be made of synthetic materials suitable for use as heart valve prosthesis leaflets in embodiments hereof including, but are not limited to polyester, polyurethane, cloth materials, nylon blends, and polymeric materials.

The sealing members 112 are formed from a suitable natural or biological graft material such as pericardium or another membranous tissue including, but not limited to intestinal submucosa. Alternatively, the sealing members 112 may be a low-porosity woven fabric, such as polyester, polyethylene terephthalate (PET), or polytetrafluoroethylene (PTFE), which creates a one-way fluid passage when attached to the stent. In one embodiment, the sealing members 112 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side.

Figure 4:
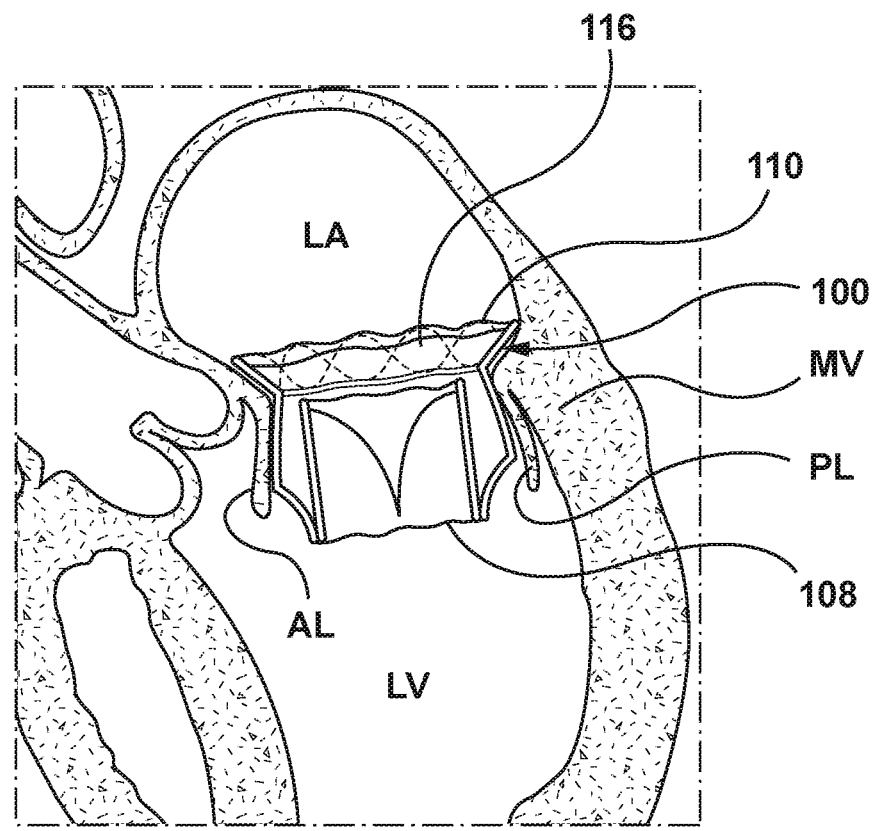
FIG. 4 is a sectional view illustration of the heart valve prosthesis of FIG. 3A implanted within an annulus of a native mitral valve.

FIG. 4 is an illustration of the heart valve prosthesis 100 implanted within a native mitral valve, which is shown in section. The heart valve prosthesis 100 is shown deployed within a native mitral valve MV, with the downstream end or outflow portion 108 extending into the left ventricle LV and the upstream end or inflow portion 108 including at least the brim 116 extending into the left atrium LA. When the heart valve prosthesis 100 is deployed within the valve annulus of a native heart valve, the valve support 104 and the anchoring member 102 radially expand within the native heart valve leaflets, posterior leaflet PL and anterior leaflet AL, of the patient's defective valve, retaining the native heart valve leaflets in a permanently open state.

A delivery system in accordance with the embodiments hereof includes a delivery catheter or device and a heart valve prosthesis (e.g., heart valve prosthesis 100 described above) mounted at a distal portion of the delivery catheter. The delivery catheter generally includes an inner shaft, an outer sheath, a deflecting segment, and a distal nosecone. The deflecting segment has a delivery state and a deflected state. When in the delivery state, the deflecting segment is generally straight and aligned with a central longitudinal axis of a distal portion of the inner shaft of the delivery catheter. When the deflecting segment is in the deflected state, the deflecting segment is deflected such that a longitudinal length of the deflecting segment in the deflected state is less than a longitudinal length of the deflecting segment in the delivery state. The deflecting segment is thus configured to laterally curve or bend away from the central longitudinal axis of the distal portion of the inner shaft or to longitudinally reduce in length, or otherwise deflect when not constrained in the delivery state. More specifically, when not constrained in the delivery state, the deflecting segment deflects such that the distal nosecone of the delivery system does not contact or damage a heart tissue or structures such as a heart chamber wall, as described below. Once the heart valve prosthesis is in a radially expanded configuration, the delivery catheter is configured to constrain the deflecting segment to return it to the delivery state for removal from the heart chamber.

Figure 5A:
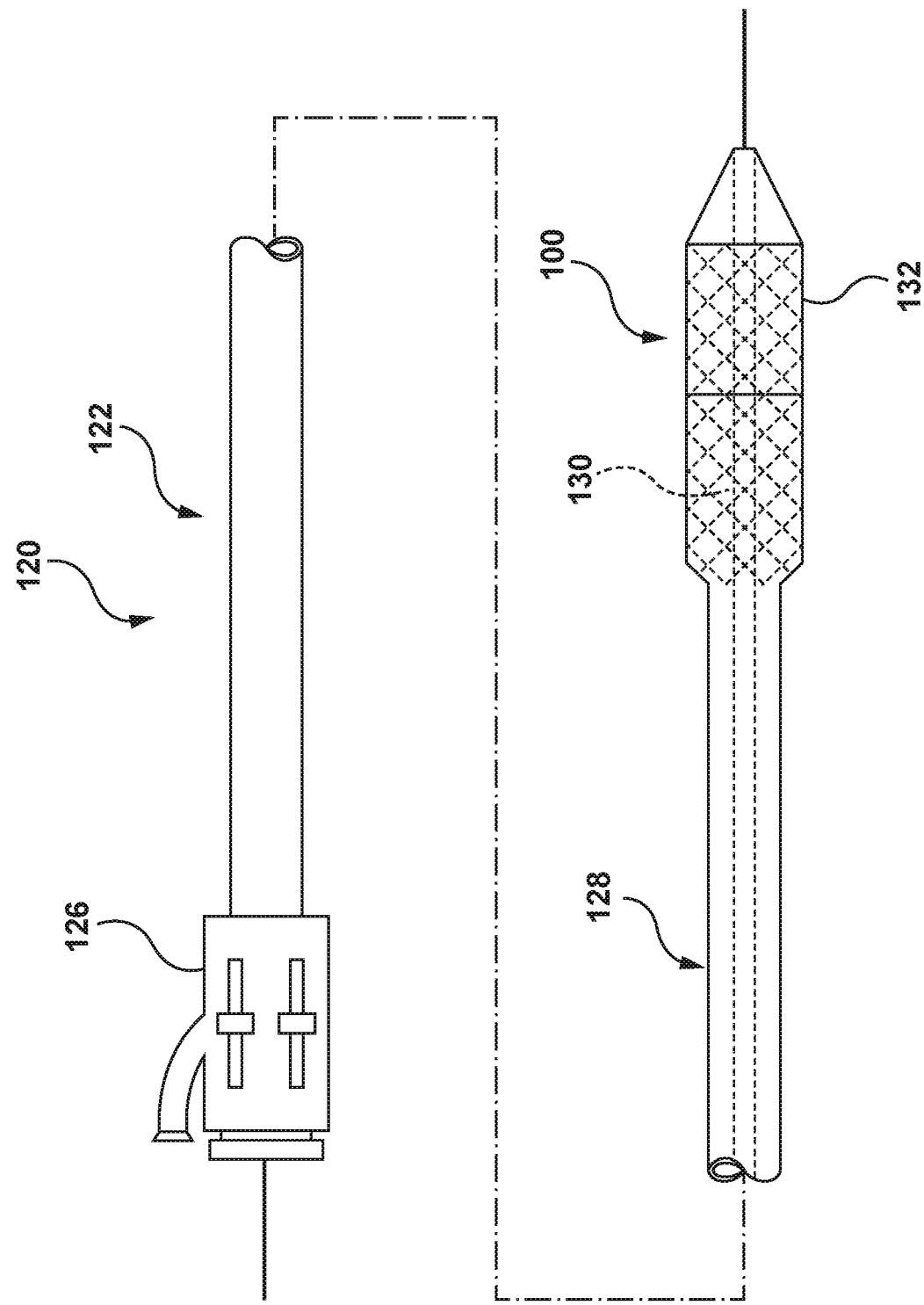
FIG. 5A is a side view illustration of a delivery catheter configured to deliver the heart valve prosthesis of FIG. 3A according to embodiments hereof, wherein the heart valve prosthesis of FIG. 3A is mounted at a distal portion thereof and the heart valve prosthesis is shown in a radially collapsed configuration for delivery.
Figure 5B:
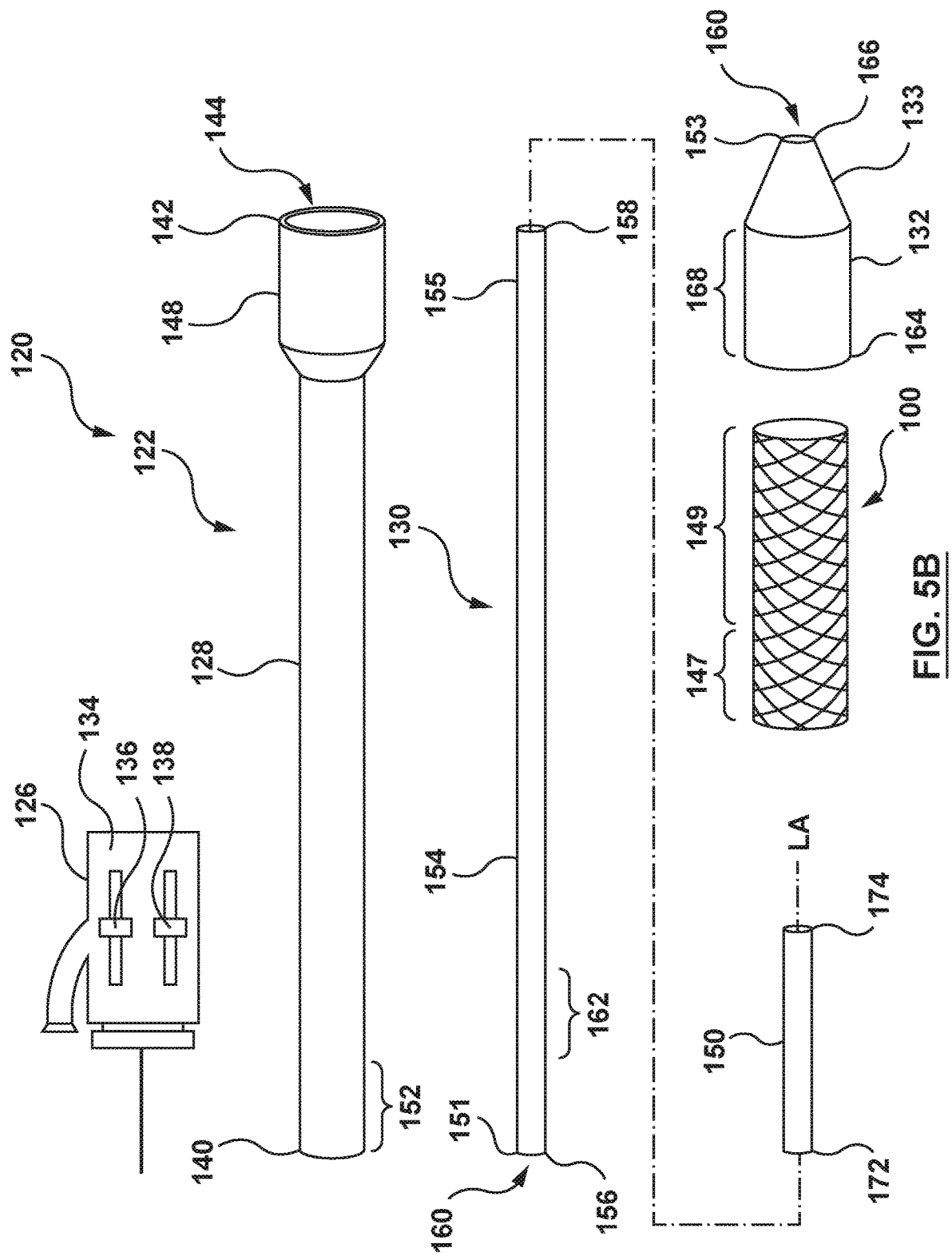
FIG. 5B is an exploded perspective view illustration of the delivery catheter of FIG. 5A.

In an embodiment shown in FIGS. 5A and 5B, a delivery system 120 includes a delivery catheter 122 and the heart valve prosthesis 100 mounted on a distal portion thereof in a radially collapsed configuration for delivery to a desired treatment location. The delivery system 120 is configured to deliver and implant the heart valve prosthesis 100 according to an embodiment of the present invention.

The delivery catheter 122 includes a handle 126, an outer sheath 128, an inner shaft assembly 130, and a distal nosecone 132 as shown in FIG. 5A. Various components of the delivery catheter 122 may assume different forms and construction based upon application needs as described in greater detail in U.S. Pat. No. 7,662,186 to Bragga et al., U.S. Pat. No. 7,740,655 to Birdsall, U.S. Pat. No. 8,579,963 to Tabor, and U.S. Pat. No. 8,926,692 to Dwork, each of which is incorporated in their entirety by reference herein, and U.S. Pat. No. 9,034,032 to McLean et al., previously incorporated by reference herein.

As shown in FIG. 5B, the handle 126 includes a housing 134, and a first actuation mechanism 136 and a second actuation mechanism 138 for interfacing by a user. The handle 126 provides a surface for convenient handling and grasping by a user, and while the handle 126 of FIGS. 5A and 5B is shown with a generally cylindrical shape, this is by way of example and not limitation as other shapes and sizes may be utilized. Further, while the handle 126 is shown with a specific style of first and second actuation mechanisms 136, 138, this is also by way of example and not limitation, and various actuation mechanisms may be utilized including, but not limited to an axially-slidable lever, a rotary rack and pinion gear, or other applicable actuation mechanisms.

Also shown in FIG. 5B, the outer sheath 128 includes a proximal end 140 and a distal end 142. The outer sheath 128 further includes a lumen 144 extending from the proximal end 140 to the distal end 144 of the outer sheath 128. The lumen 144 is sized to slidably receive the inner shaft assembly 130. A distal portion 148 of the outer sheath 128 is configured to retain a first portion 147 of the heart valve prosthesis 100 in the radially collapsed configuration for delivery to a desired treatment location. In an embodiment, the first portion 147 is the inflow portion 110 of the heart valve prosthesis 100, shown in FIGS. 3A-3C and 4, and includes the brim 116 of the heart valve prosthesis 100. The outer sheath 128, including the distal portion 148, is further configured to constrain a deflecting segment 150 of the inner shaft assembly 130 in a delivery state, with the deflecting segment 150 generally straightened and aligned with a central longitudinal axis LA of a distal portion 155 of the inner shaft 154 of the delivery catheter 122 when disposed therein, as will be described in greater detail below. While the distal portion 148 is described herein as a distal portion of the outer sheath 128, in an embodiment the distal portion 148 may be a separate component, such as a capsule, coupled to the distal end 142 of the outer sheath 128, as described in U.S. Pat. No. 8,926,692 to Dwork, previously incorporated in its entirety by reference herein. Moreover, although the outer sheath 128 is described herein as a single component, this is by way of example and not limitation, and the outer sheath 128 may include multiple components such as, but not limited to proximal and distal shafts or other components suitable for the purposes described herein. The proximal end 140 of the outer sheath 128 is configured for fixed connection to the handle 126. In an embodiment, the proximal end 140 of the outer sheath 128 may extend proximally into the housing 134 of the handle 126 and a proximal portion 152 of the outer sheath 128 may be operably coupled to the first actuation mechanism 136 of the handle 126. The proximal portion 152 is operably coupled to the first actuation mechanism 136 such that movement of the first actuation mechanism 136 causes the outer sheath 128 and the distal portion/capsule 148 to move relative to the inner shaft assembly 130 and the handle 126. However, if the first actuation mechanism 136 is not moved and the handle 126 is moved, the outer sheath 128 moves with the handle 126, not relative to the handle 126. The outer sheath 128 may be constructed of materials such as, but not limited to polyurethane, polyether block amide (PEBA), polyamide, polyether block copolymer, polyethylene, or other materials suitable for the purposes of the present disclosure. The proximal portion 152 of the outer sheath 128 may be coupled to the first actuation mechanism 136, for example, and not by way of limitation by adhesives, welding, clamping, linkages or other coupling methods as appropriate.

The inner shaft assembly 130 extends within the lumen 144 of the outer sheath 128. The inner shaft assembly 130 includes a lumen 160 extending from a proximal end 151 to a distal end 153 of the inner shaft assembly 130, as shown in FIG. 5B. The lumen 160 is configured to receive auxiliary components, such as a guidewire. The inner shaft assembly 130 includes a tubular inner shaft 154, the deflecting segment 150, and the distal nosecone 132. In embodiments hereof, the distal nosecone 132 may alternatively be referred to as a distal tip. The inner shaft 154 is coupled to the deflecting segment 150, and the deflecting segment 150 is coupled to the distal nosecone 132. Although the inner shaft assembly 130 is described herein as including the separate components of the inner shaft 154, the deflecting segment 150, and the distal nosecone 132, one or both of the deflecting segment 150 and the distal nosecone 132 may alternatively be integral with or an extension of the inner shaft 154. At least a portion 162 of the inner shaft assembly 130 is configured to extend within the handle 126 to be operably connected to the second actuation mechanism 138 of the handle 126. The portion 162 is coupled to the second actuation mechanism 138 such that movement or actuation of the second actuation mechanism 138 causes the inner shaft assembly 130 to move relative to the outer sheath 128 and the handle 126. However, if the second actuation mechanism 138 is not moved and the handle 126 is moved, the inner shaft assembly 130 moves with the handle 126, not relative to the handle 126. The inner shaft assembly 130 may be constructed of materials such as, but not limited to polyurethane, polyether block amide (PEBA), polyamide polyether block copolymer, polyethylene, or other materials suitable for the purposes of the present disclosure. The portion 162 of the inner shaft assembly 130 may be operably coupled to the second actuation mechanism 138, for example, and not by way of limitation by adhesives, welding, clamping, linkages or other coupling methods as appropriate.

The inner shaft 154 includes a proximal end 156 and a distal end 158, as shown in FIG. 5B. The inner shaft 154 further defines a proximal portion of the lumen 160 extending from the proximal end 156 to the distal end 158 of the inner shaft 154. The distal end 158 of the inner shaft 154 is coupled to a proximal end 172 of the deflecting segment 150. The inner shaft 154 is configured to transmit movement of the inner shaft 154 to the deflecting segment 150.

The distal nosecone 132 includes a distal portion of the lumen 160. The distal portion of the lumen 160 extends distally from a proximal end 164 to a distal end 166 of the distal nosecone 132, as shown in FIG. 5B. The distal nosecone 132 includes a frusto-conical tip 133 disposed at a distal portion thereof. The frusto-conical tip 133 permits atraumatic advancement of the delivery catheter 122 through the often tortuous vasculature. In an embodiment, a proximal portion 168 of the distal nosecone 132 is configured to retain a second portion 149 of the heart valve prosthesis 100 in a radially collapsed configuration therein, as shown in FIG. 3B, for delivery to a desired treatment location. In an embodiment, the second portion 149 includes the outflow portion 108 of the heart valve prosthesis 100, shown in FIGS. 3A-3C and 4. The distal nosecone 132 is coupled to a distal end 174 of the deflecting segment 150.

Figure 6A:
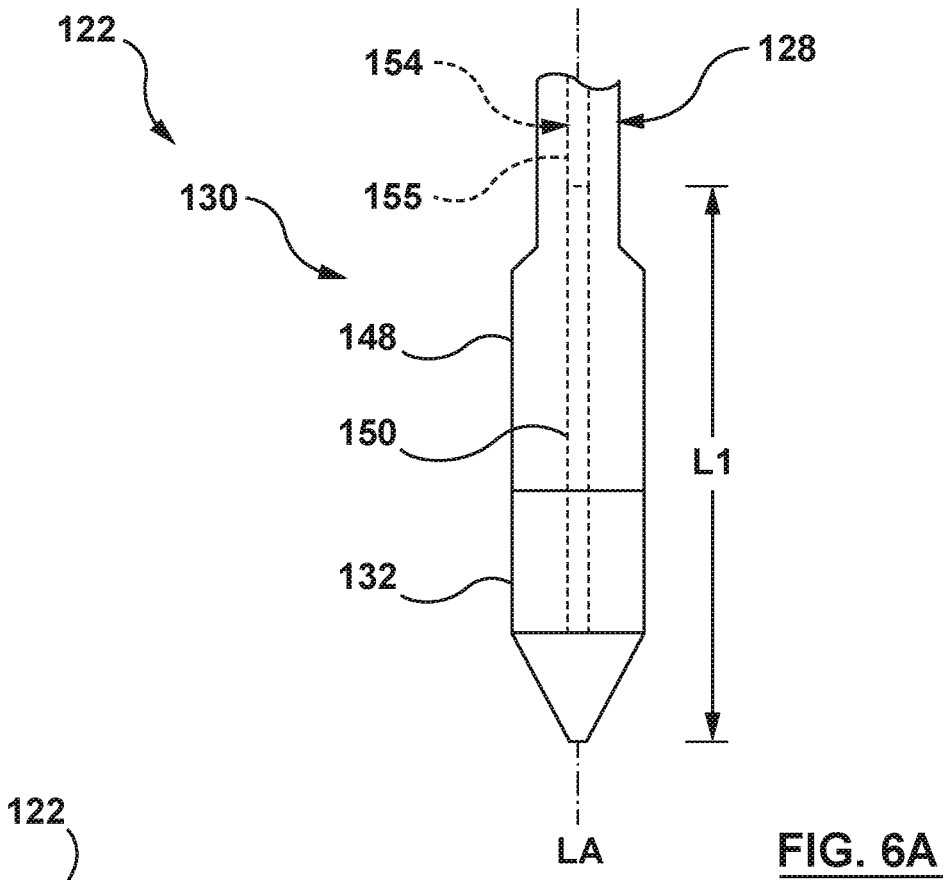
FIG. 6A is a side view illustration of a deflecting segment of the delivery catheter of FIG. 5A, wherein the deflecting segment is in a delivery state in accordance with an embodiment hereof, and wherein the heart valve prosthesis has been omitted for clarity.
Figure 6B:
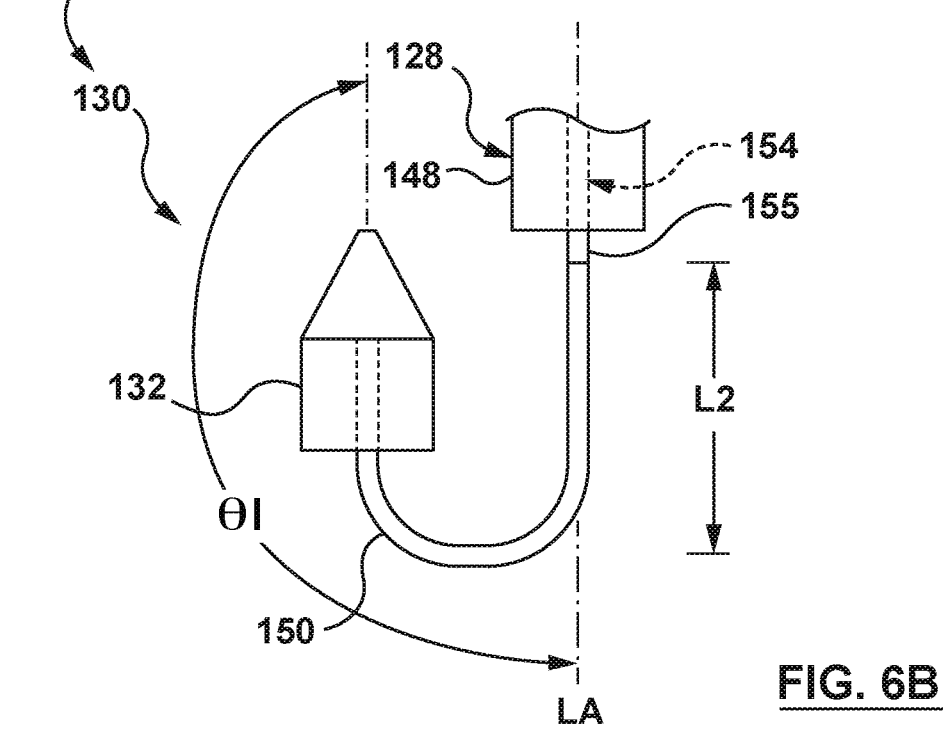
FIG. 6B is a side view illustration of the deflecting segment of FIG. 6A, wherein the deflecting segment is in a deflected state in accordance with an embodiment hereof, and wherein the heart valve prosthesis has been omitted for clarity.

The deflecting segment 150 of the inner shaft assembly 130 according to an embodiment hereof is shown in FIGS. 5B, 6A and 6B. The deflecting segment 150 is a generally tubular element and includes an intermediate portion of the lumen 160. The intermediate portion of the lumen 160 extends from the proximal end 172 to the distal end 174 of the deflecting segment 150, as shown in FIG. 5B. Accordingly, the deflecting segment 150 is disposed between the inner shaft 156 and the distal nosecone 132, with the proximal end 172 of the deflecting segment 150 coupled to the distal end 158 of the inner shaft 154 and the distal end 174 of the deflecting segment 150 coupled to the distal nosecone 132.

The deflecting segment 150 has the delivery state and a deflected state. When in the delivery state, the deflecting segment 150 is generally aligned with the central longitudinal axis LA of the distal portion 155 of the inner shaft 154, as shown in FIG. 6A. It will be understood that the heart valve prosthesis 100 has been omitted from FIGS. 6A and 6B for clarity.

The deflecting segment 150 is configured to bend or curve or laterally move away from the central longitudinal axis LA to the deflected state with an angle of deflection θ1, as shown in FIG. 6B, when not constrained in the delivery state. Thus, the deflecting segment 150 transitions from the delivery state to the deflected state by bending or curving a portion of the deflecting segment 150 laterally away from the central longitudinal axis LA of the distal portion 155 of the inner shaft 154. The deflecting segment 150 may be constrained in the delivery state by either a heart valve prosthesis that surrounds the deflecting segment 150 when in the radially collapsed configuration thereabout, or by the distal portion 148 of the outer sheath 128 surrounding the deflecting segment 150 when the deflecting segment 150 is disposed therein. In another embodiment, the deflecting segment 150 may additionally, or alternatively, be constrained by ties that would rip/release upon return of the deflecting segment to the deflected state, or due to tension/shear when moving/translating/sliding the deflecting segment relative to the prosthesis. As disclosed here, deflection of deflecting segment and distal nosecone when unconstrained could be achieved by nitinol or a similar superelastic material, a stiff strip of material on one side of the deflecting segment, or designed in via coiling or braiding of a suitable wire that forms the deflecting segment. In an embodiment, in the deflected state, the deflecting segment 150 is configured to curve or bend into a substantially U-shape with an angle of deflection θ1 of substantially 180° following the release of the heart valve prosthesis 100 (not shown in FIGS. 6A and 6B) at a desired treatment site of, for e.g., a native mitral valve, and thereby to extend the distal nosecone 132 lateral of the central longitudinal axis LA of the distal portion 155 of the inner shaft 154, such that the distal nosecone 132 does not contact or damage myocardial tissue, for e.g., a heart wall of the left ventricle, as the inner shaft assembly 130 is advanced. While FIG. 6B shows the distal segment 150 laterally deflecting in a specific direction from the central longitudinal axis LA, this is not meant to be limiting, and the distal segment 150 may be configured to laterally deflect in any direction.

When the deflecting segment 150 is in a delivery state, as shown in FIG. 6A, the deflecting segment 150 and the distal nosecone 132 together have a first axial length L1 measured along the central longitudinal axis LA of the distal portion 155 of the inner shaft 154. In contrast when the deflecting segment 150 is in a deflected state, as shown in FIG. 6B with the distal nosecone 132 laterally displaced from the central longitudinal axis LA, the deflecting segment 150 has a second axial length L2 measured along the central longitudinal axis LA of the distal portion 155 of the inner shaft 154, wherein the first axial length L1 with the deflecting segment 150 in the delivery state is greater than the second axial length L2 with the deflecting segment 150 in the deflected state. In an embodiment when the delivery system 120 is used to deploy the heart valve prosthesis 100 within a native mitral valve, the distal nosecone 132 may be described to generally extend away from an apex of the left ventricle when the deflecting segment 150 is in the deflected state and toward the apex of the left ventricle when the deflecting segment 150 is in the delivery state.

The deflecting segment 150 is formed of a shape memory material with a pre-set shape to return to the deflected state. The shape-memory of the deflecting segment 150 may be accomplished using known shape-setting techniques and materials, non-limiting examples of which include the deflecting segment 150 formed from a polymer shaft and heat-setting of the polymer shaft in a deflected shape, the deflecting segment 150 formed of a nickel-titanium alloy (e.g. NITINOL) shaft, the deflecting segment 150 formed of a polymer shaft with a nickel-titanium alloy (e.g. NITINOL), braiding disposed on the outer surface of the polymer shaft, or the addition of a thermal-memory strip to the deflecting segment 150. In embodiments hereof, a deflecting segment may be of a polymeric tubing having a strip of a general stiff material with good elastic properties attached thereto, with the strip being sufficiently stiff and elastic to cause a suitable deflection. In other embodiments, a deflecting segment may be a tube formed from coil/braiding techniques to force a preferred shape, such as a U or L shape, when unconstrained. The deflecting segment 150 may be coupled to the inner shaft 154 and the distal nosecone 132 by methods such as, but not limited to adhesives, bonding, fusing, welding, or any other suitable method.

Figure 7A:
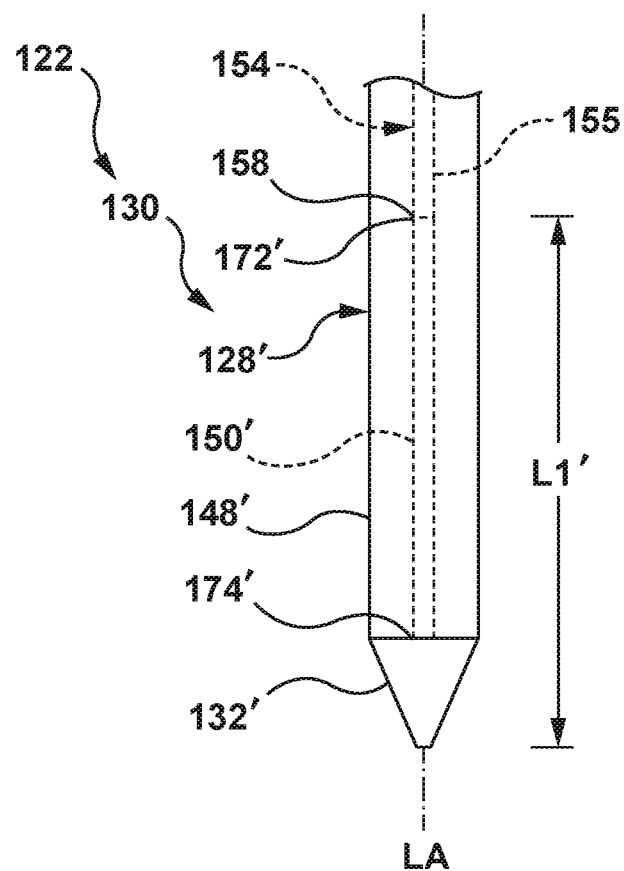
FIG. 7A is a side view illustration of a deflecting segment of the delivery system of FIG. 5A, wherein the deflecting segment is in a delivery state in accordance with another embodiment hereof, and wherein the heart valve prosthesis has been omitted for clarity.
Figure 7B:
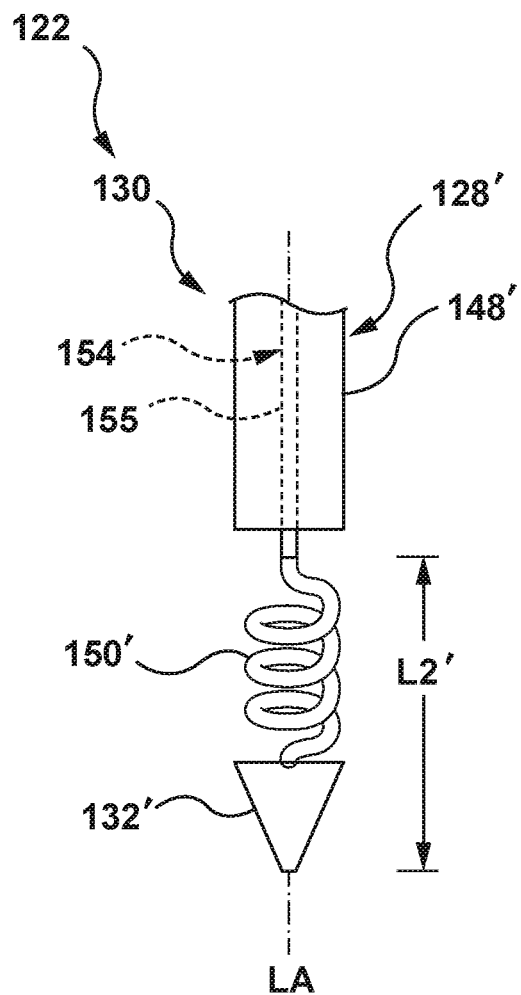
FIG. 7B is a side view illustration of the deflecting segment of FIG. 7A, wherein the deflecting segment is in a deflected state in accordance with another embodiment hereof, and wherein the heart valve prosthesis has been omitted for clarity.

A deflecting segment 150' of the inner shaft assembly 130 according to another embodiment hereof is shown in FIGS. 7A and 7B. The deflecting segment 150' is similar to the deflecting segment 150 described previously. Therefore similar construction and alternatives will not be repeated. The deflecting segment 150' includes a proximal end 172' and a distal end 174', and further has a substantially straight tubular shape when held in a delivery state within a distal portion 148' of an outer sheath 128', as shown in FIG. 7A. Similar to the deflecting segment 150 described previously, the deflecting segment 150' is constrained in the delivery state by the heart valve prosthesis 100 (omitted from FIGS. 7A and 7B for clarity), which surrounds the deflecting segment 150' when the heart valve prosthesis 100 is in the radially collapsed configuration thereabout. When in the delivery state, the deflecting segment 150' has a substantially straightened profile and is generally aligned with the central longitudinal axis LA of the distal portion 155 of the inner shaft 154 of the delivery catheter 122, as shown in FIG. 7A. The deflecting segment 150' is configured to axially deflect (retract) along the central longitudinal axis LA to the deflected state of FIG. 7B when not constrained in the delivery state within the distal portion 148' of the outer sheath 128', as shown in FIG. 7B. Thus, the deflecting segment 150' transitions from the delivery state to the deflected state by proximally collapsing a portion of the deflecting segment 150' along the central longitudinal axis LA of the distal portion 155 of the inner shaft 154. The deflecting segment 150' in a deflected state collapses to an accordion, coiled, folded or wavy shape when not constrained in the delivery state by the heart valve prosthesis 100 in the radially collapsed configuration thereabout or the distal portion 148' of the outer sheath 128', as shown in FIG. 7B. More precisely, the deflecting segment 150' is configured to proximally fold, crease or retract such that an axial or longitudinal length' of the deflecting segment 150' in the deflected state is reduced along the central longitudinal axis LA of the distal portion 155 of the inner shaft 154, when the heart valve prosthesis 100 is released from the delivery catheter 122. Accordingly, a distal nosecone 132' of the delivery catheter 122 is proximally retracted by the deflecting segment 150' in the deflected state and thus the distal nosecone 132' will not contact or damage a heart wall when the inner shaft assembly 130 is distally advanced.

When the deflecting segment 150' is in a delivery state, as shown in FIG. 7A, the deflecting segment 150' and the distal nosecone 132' have a combined first axial length L1' measured along the central longitudinal axis LA of the distal portion 155 of the inner shaft 154. When the deflecting segment 150' is in a deflected state, as shown in FIG. 7B, the deflecting segment 150' and the distal nosecone 132' have a combined second axial length L2' measured along the central longitudinal axis LA of the distal portion 155 of the inner shaft 154, wherein the first axial length L1' with the deflecting segment 150' in the delivery state is greater than the second axial length L2' with the deflecting segment 150' in the deflected state. The deflecting segment 150' is formed of a shape memory material and by methods described with respect to the deflecting segment 150 of FIGS. 6A and 6B.

It will be understood that when the deflecting segment 150 of FIGS. 5B, 6A and 6B and the deflecting segment 150' of FIGS. 7A and 7B are in the delivery state, each deflecting segment 150, 150' is sized to fit within the heart valve prosthesis 100 in the radially compressed configuration. In other words, an outside diameter of the deflecting segment 150, 150' in the delivery state is less than or substantially equal to the inside diameter of the heart valve prosthesis 100 in the radially compressed configuration. By "substantially equal" it is meant that an outer surface of the deflecting segment 150, 150' may be in contact with an inner surface of the heart valve prosthesis 100. Further, the deflecting segment 150 is sized to fit within the outer sheath 128 when in the delivery state, but not when in the deflected state. The drawings are not to scale.

With an understanding of the components of the delivery system 120, the interaction of the various components of the delivery system 120 are now described. Referring back to FIGS. 5A and 5B, a deflecting segment 150 of a delivery catheter 122 is manipulated to the delivery state and constrained in the delivery state by a heart valve prosthesis 100, such as the heart valve prosthesis 100, that surrounds the deflecting segment 150 when in the radially collapsed configuration thereabout.

The delivery system 120 is advanced to a treatment site of a native heart valve to position the heart valve prosthesis within an annulus of the native heart valve. Thereafter, an outer sheath 128 of the delivery catheter 122 may be proximally retracted to release at least a first portion of the heart valve prosthesis and to permit the first portion to radially expand into engagement with the native heart valve.

Thereafter, an inner shaft assembly 130 of the delivery catheter 122 may be distally advanced to release a second portion of the heart valve prosthesis and to permit the second portion to radially expand into engagement with the native heart valve. As the heart valve prosthesis radially expands, constraining forces on the deflecting segment 150 are removed and the deflecting segment 150 transitions from the delivery state of FIG. 6A to the deflected state of FIG. 6B, with a corresponding reduction in an axial length of the deflecting segment and a nosecone of the delivery catheter 122 from a delivery length L1 to a shorter deflected length L2. Due to the shorter deflected length L2, with the deflecting segment deflecting the nosecone 132 lateral of the central longitudinal axis LA of a distal portion of an inner shaft of the delivery catheter 122, potential myocardial damage by the distal nosecone 132 from continued distal advancement of the delivery catheter 122 may be prevented. Moreover, deployment of the heart valve prosthesis may be made quicker by eliminating a clinician's concerns and motivation to proceed slowly to prevent potential myocardial damage by the distal nosecone 132 during distal movement of the delivery catheter 122, as the potential for damage is prevented by the shorter longitudinal length L2 thereof.

Once the heart valve prosthesis is positioned and radially expanded within the native heart valve, the outer sheath 128 is distally advanced. The inner shaft assembly 130 is then proximally retracted and as the deflecting segment 150 is received within the outer sheath 128, the deflecting segment 150 straightens or unbends. Thus, as the deflecting segment 150 is drawn within the outer sheath 128, the outer sheath 128 applies constraining forces to the deflecting segment 150 such that the deflecting segment 150 transitions from the deflected state of FIG. 6B to the delivery state of FIG. 6A.

FIGS. 8-13 are sectional cut-away views of a heart HE illustrating a transseptal approach method for delivering and positioning a heart valve prosthesis 100 using a delivery system 120 of FIG. 5A in accordance with an embodiment hereof.

Figure 8:
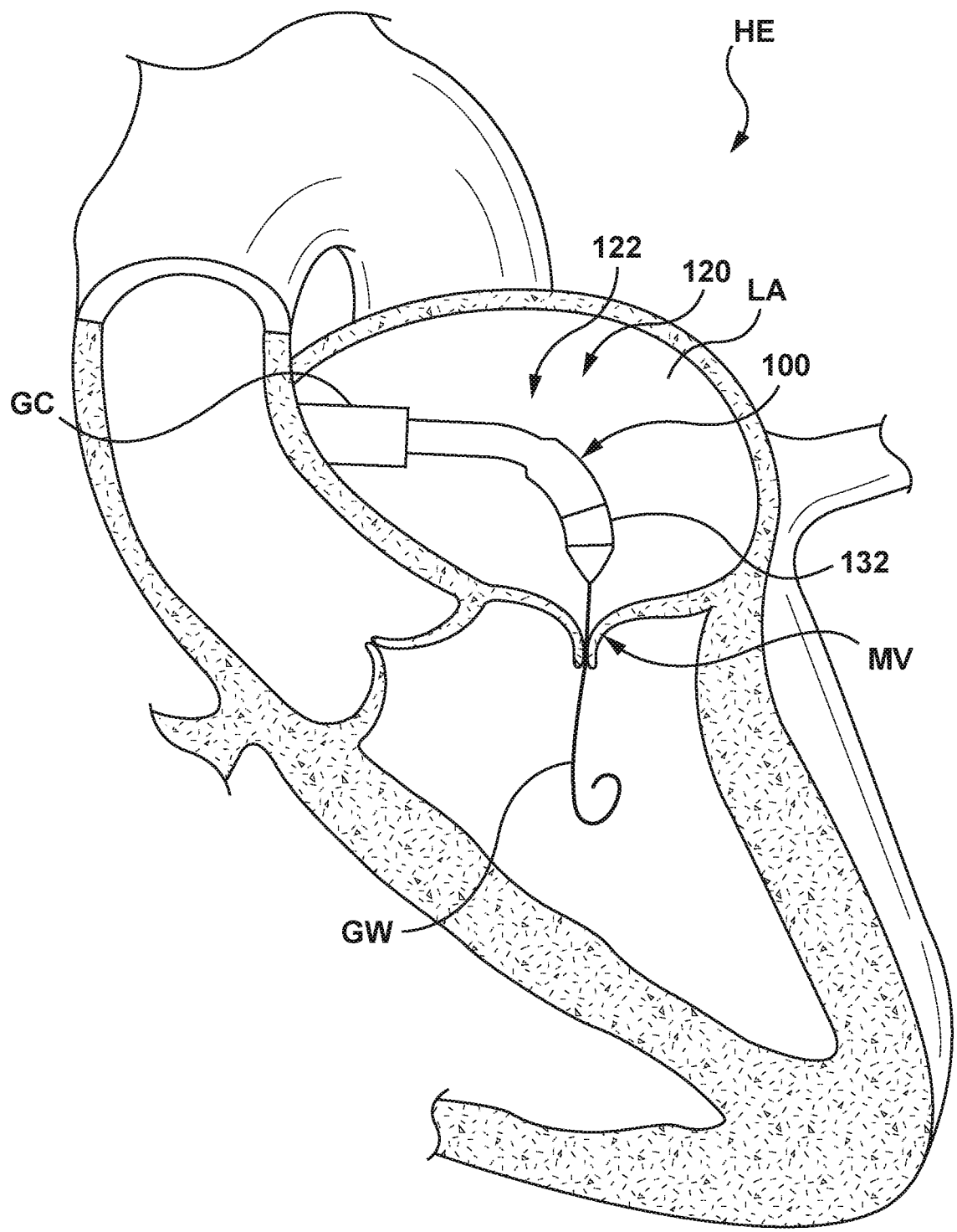
FIG. 8 is an illustration of the delivery catheter of FIG. 5A in situ, the delivery catheter being positioned in the left atrium via a transseptal approach, wherein the heart valve prosthesis is in a radially collapsed configuration for delivery.

With reference to FIG. 8, a delivery catheter 122 is shown after having been introduced into the vasculature via a percutaneous entry point, a.k.a the Seldinger technique, and tracked through the vasculature into a left atrium LA of a heart HE so that the distal nosecone 132 is positioned proximate a native mitral valve MV. Intravascular access to the right atrium RA may be achieved via a percutaneous access site to femoral venous access up to the inferior venal cava, or other known access routes. Thereafter, a guidewire GW is advanced through the circulatory system, eventually arriving at the heart HE. The guidewire GW is directed into the right atrium, traverses the right atrium and is made to traverse, with the aid of a transseptal needle or pre-existing hole, an atrial septum, thereby entering the left atrium LA. Once the guidewire GW is positioned, the endoluminal entry port and the atrial septum are dilated to permit entry of a guide catheter GC into the left atrium LA. Thereafter, the delivery catheter 122 is advanced over the guidewire GW and through a delivery shaft of the guide catheter GC into the left atrium LA through the punctured atrial septum and positioned proximate or upstream to the native mitral valve MV. Although described as a transfemoral antegrade approach for percutaneously accessing the mitral valve MV, the heart valve prosthesis 100 may be positioned within the desired area of the heart HE via different methods such as a transseptal antegrade approach via a thoracotomy for accessing the mitral valve MV. In addition, although described with the use of the guide catheter GC and the guidewire GW, in another embodiment hereof the delivery catheter 122 may access the left atrium LA without the use of the guidewire GW and/or the guide catheter GC.

Figure 9:
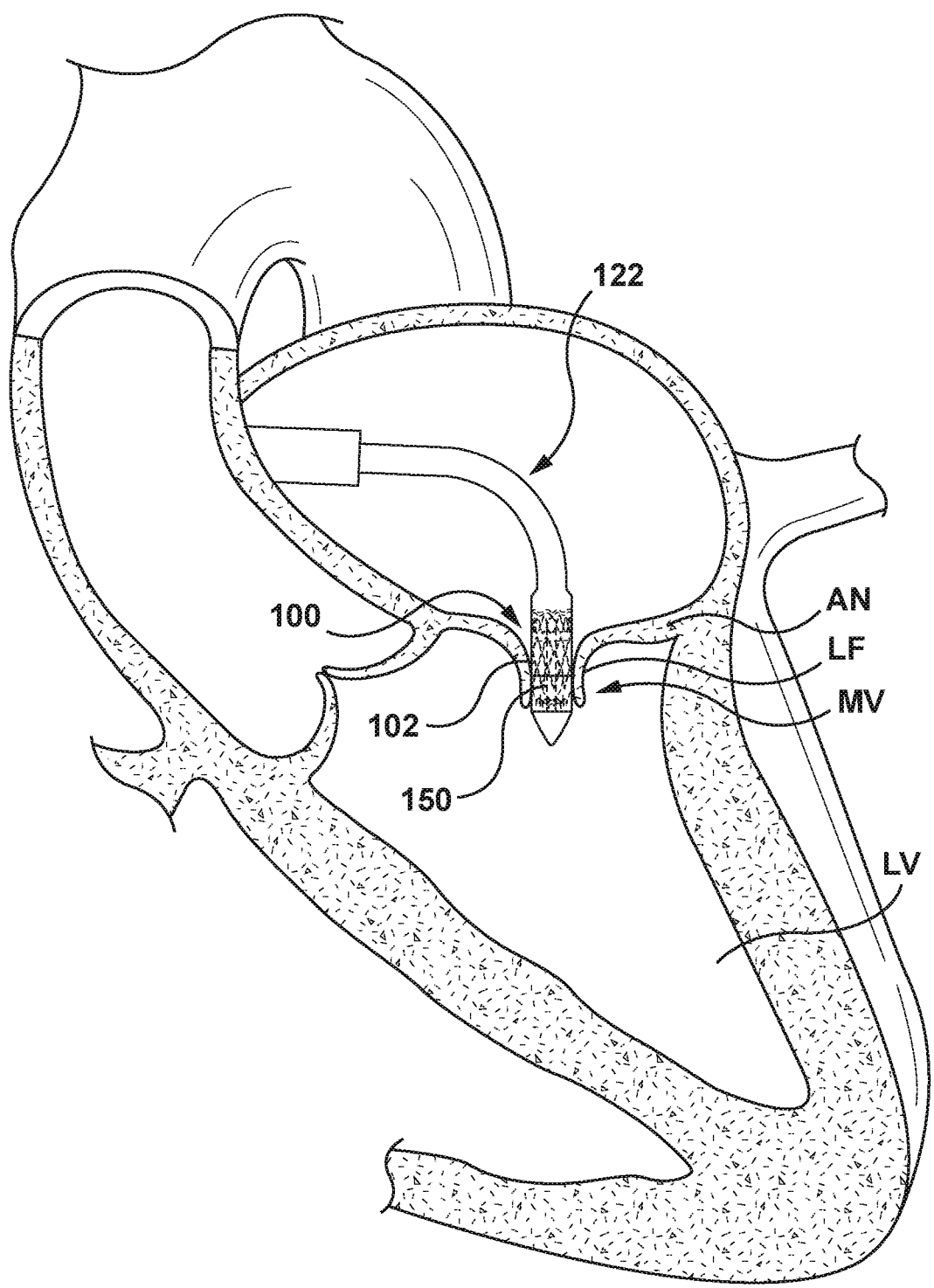
FIG. 9 is an illustration of the delivery catheter of FIG. 5A in situ, wherein the heart valve prosthesis is in the radially collapsed configuration for delivery and an anchoring member of the heart valve prosthesis is positioned within a native mitral valve.

With reference to FIG. 9, the delivery catheter 122 is distally advanced into proximity to and/or apposition with an annulus AN and/or leaflets LF of the native mitral valve MV. The distal nosecone 132 is advanced into the left ventricle LV until the heart valve prosthesis 100 is centered at the native mitral valve MV. The guidewire GW (not visible is FIG. 9) may then be proximally retracted from the delivery catheter 122 to at least a position proximal of the deflecting segment 150.

Figure 10:
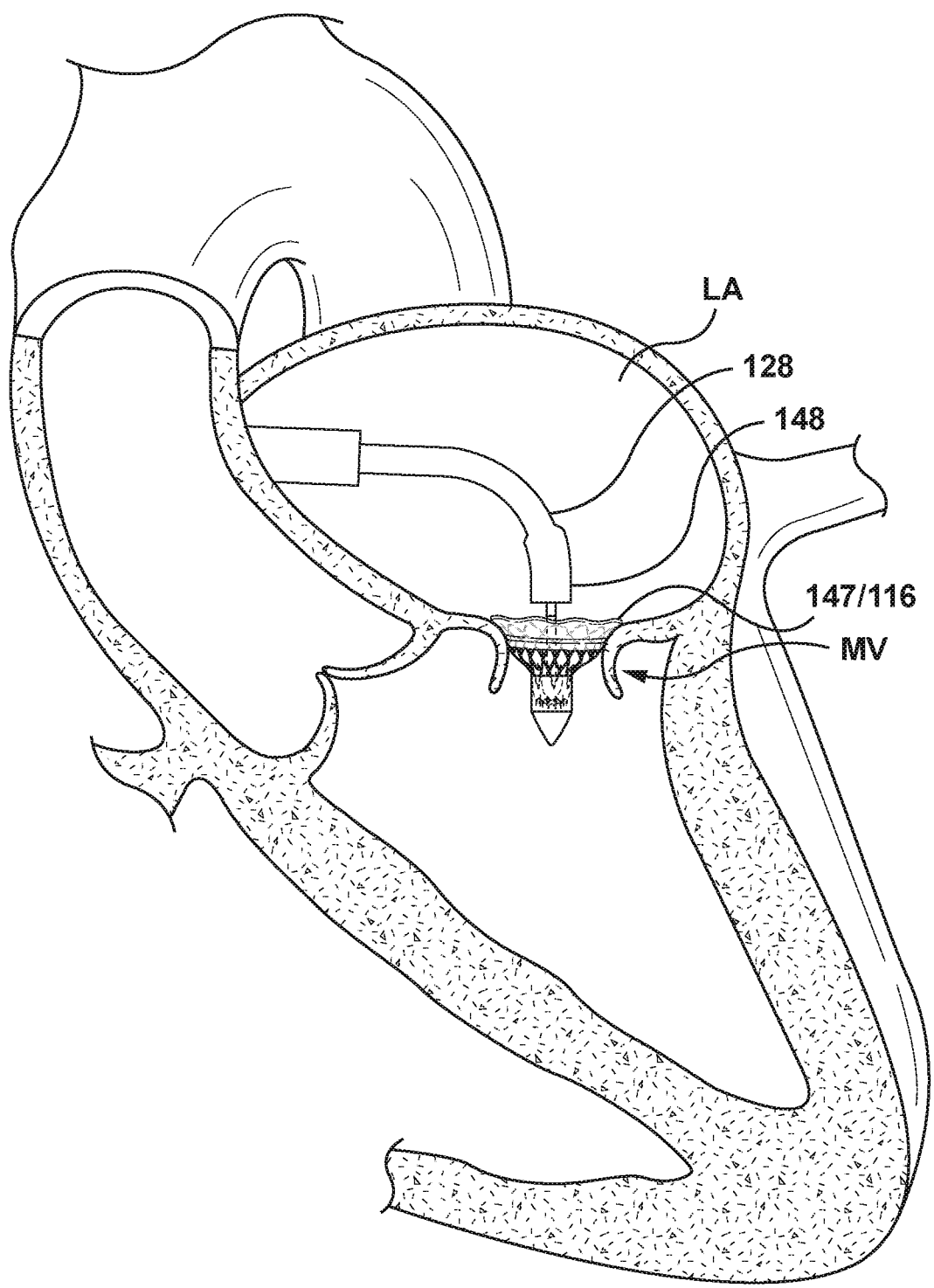
FIG. 10 is an illustration of the delivery catheter of FIG. 5A in situ, wherein an outer sheath has been retracted to deploy a first portion of the heart valve prosthesis, and a deflecting segment of the delivery catheter is distally extending from a distal end of the outer sheath.

Referring to FIG. 10, once the heart valve prosthesis 100 is positioned within the native mitral valve MV, the first actuation mechanism 136 (not shown in FIGS. 8-13) of the handle 126 (not shown in FIGS. 8-13) is manipulated such that the outer sheath 128 is proximally retracted to release the first portion 147, including at least the brim 116 of the heart valve prosthesis 100. When released from the distal portion/capsule 148, the first portion 147 of the heart valve prosthesis 100 radially expands at an atrial portion of the native mitral valve MV. With the first portion 147 radially expanded, the delivery catheter 122 is distally advanced such that the first portion 147 engages tissue at the atrial area of the native mitral valve MV, as shown in FIG. 10.

Figure 11:
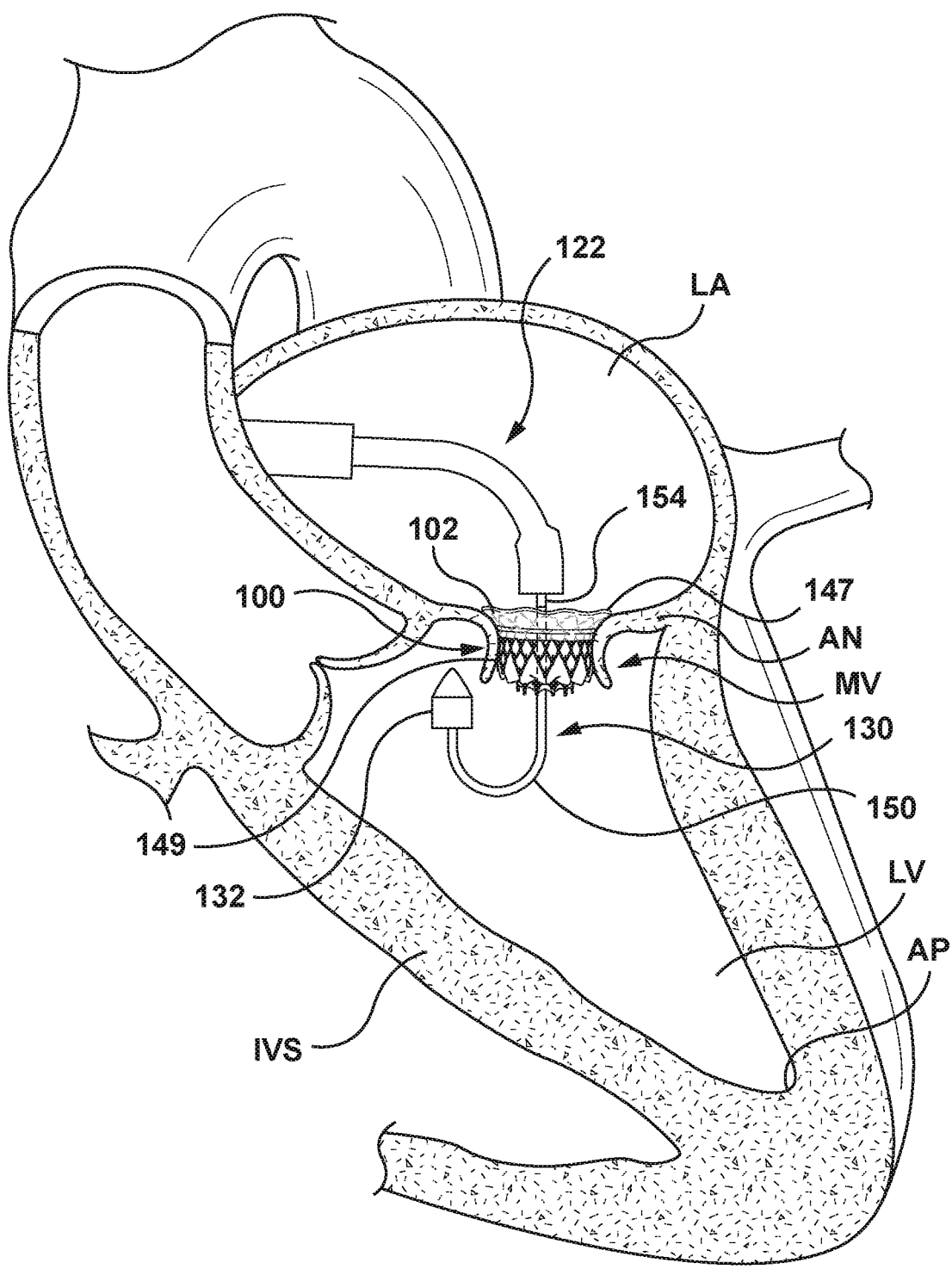
FIG. 11 is an illustration of the delivery catheter of FIG. 5A in situ, wherein an inner shaft assembly has been advanced to deploy a second portion of the heart valve prosthesis, and the deflecting segment of the delivery catheter is in a deflected state.

Referring to FIG. 11, with the first portion 147 engaged with tissue of the left atrium LA, the second actuation mechanism 138 (not shown in FIGS. 8-13) of the handle 126 (not shown in FIGS. 8-13) is now manipulated to distally advance the inner shaft assembly 130 to release the second portion 149 of the heart valve prosthesis 100 from the delivery distal nosecone 132 of the catheter 122. Once released, the second portion 149 of the heart valve prosthesis 100 expands radially such that the anchoring member 102 engages tissue at the annulus AN of the native mitral valve MV. As the second portion 149 of the heart valve prosthesis 100 radially expands, constraining forces imparted on the deflecting segment 150 by the heart valve prosthesis 100 in the radially collapsed configuration are removed. No longer constrained, the deflecting segment 150 transitions from the delivery state to the deflected state such that, in the embodiment shown, the distal nosecone 132 is displaced lateral of the inner shaft 154 with the deflecting segment 150 curving into a substantially U-shape.

Figure 12:
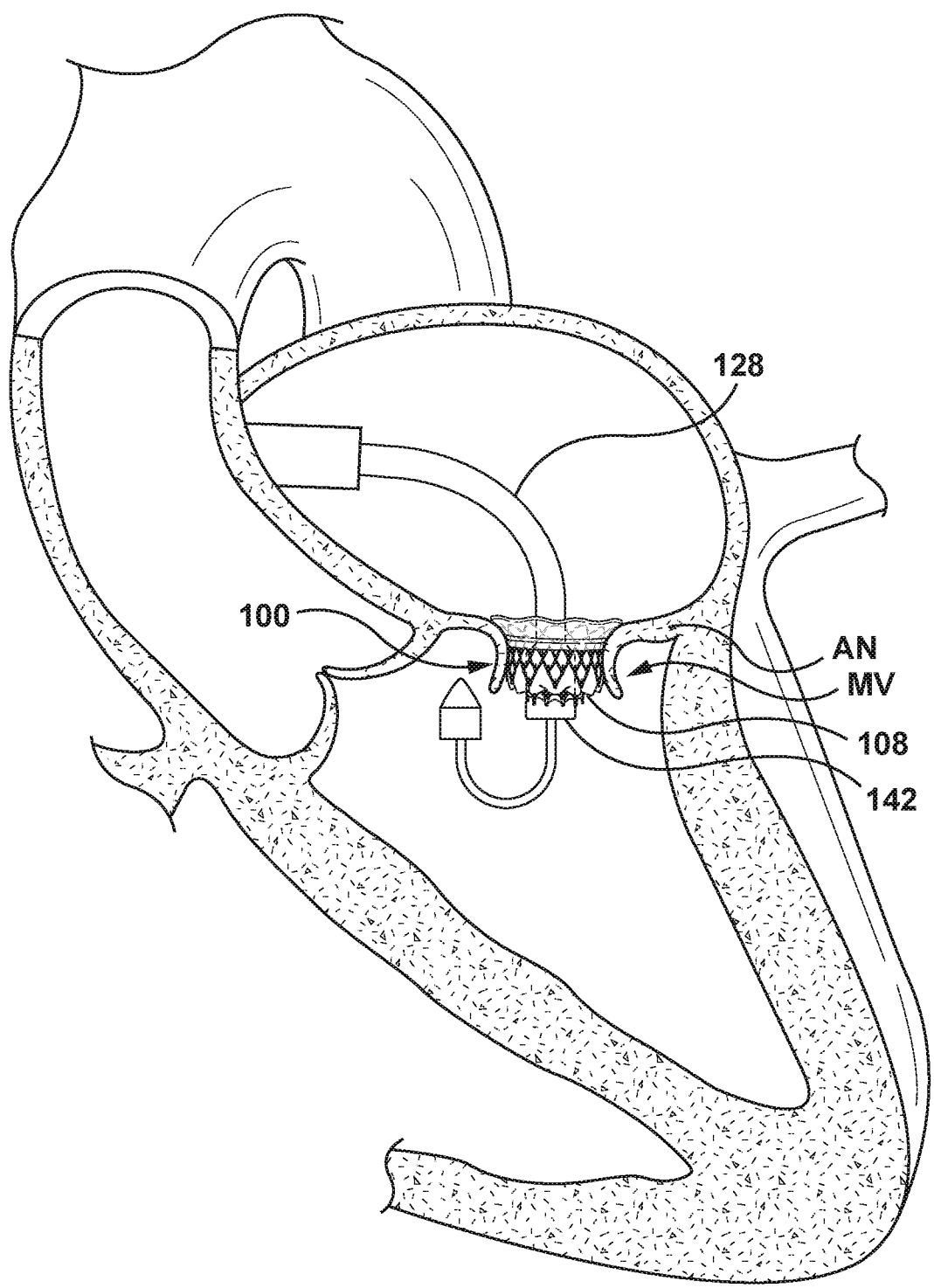
FIG. 12 is an illustration of the delivery catheter of FIG. 5A in situ, wherein the outer sheath has been distally advanced through the heart valve prosthesis.

Once the heart valve prosthesis 100 is in the radially expanded configuration within the annulus AN of the native mitral valve MV, the first actuation mechanism 136 (not shown in FIGS. 8-13) of the handle 126 (not shown in FIGS. 8-13) is manipulated to distally advance the outer sheath 128 and position the distal end 142 of the outer sheath 128 in apposition with the outflow portion 108 of the heart valve prosthesis 100, as shown in FIG. 12.

Figure 13:
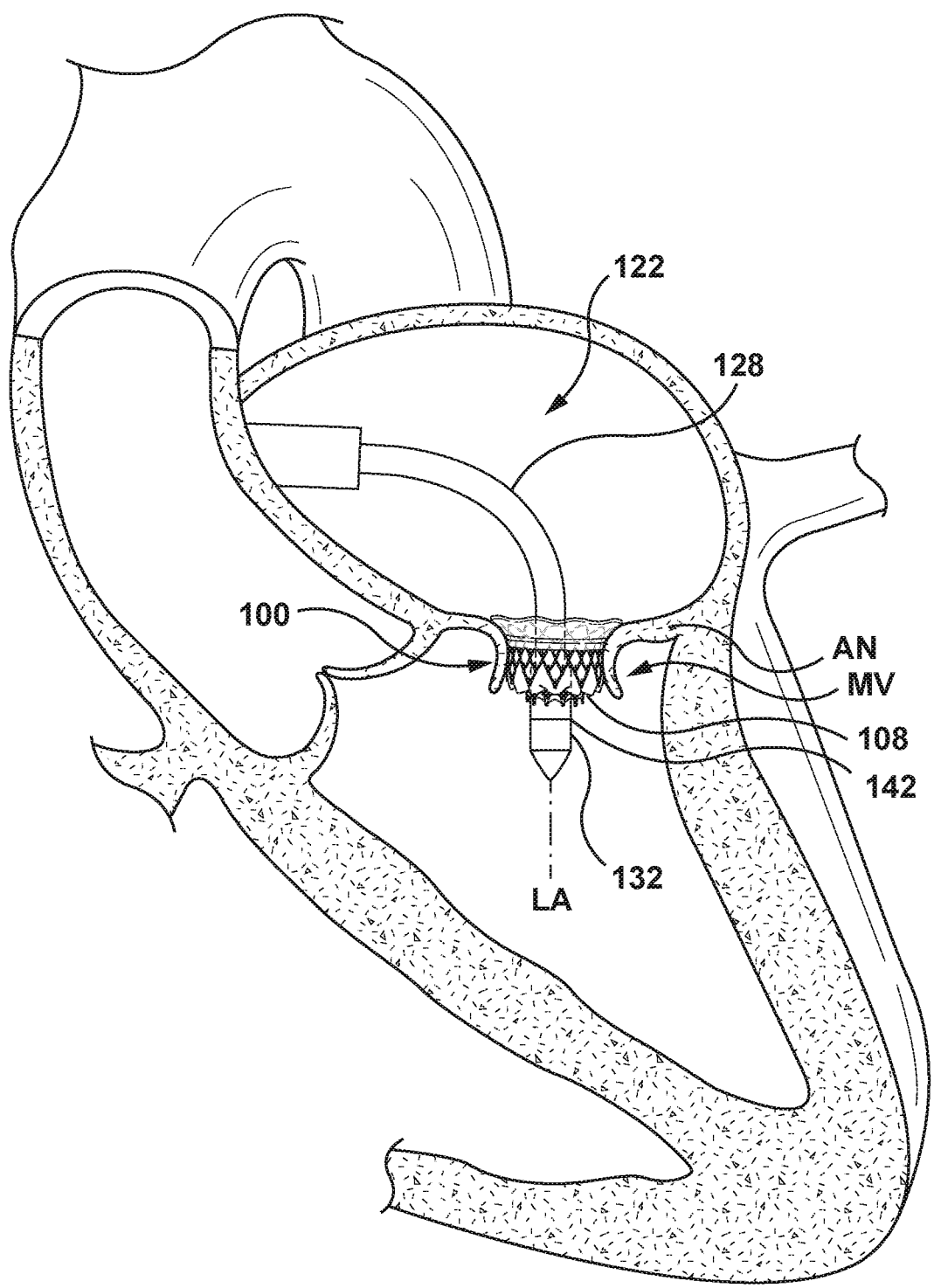
FIG. 13 is an illustration of the delivery catheter of FIG. 5A in situ, wherein the inner shaft assembly has been proximally retracted and the deflecting segment is in a delivery state within the outer sheath.
Figure 14E:
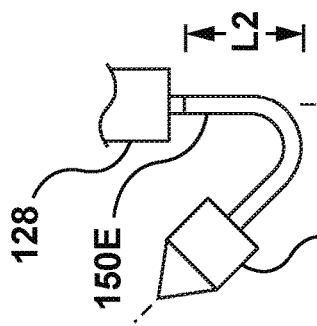
FIGS. 14A-14E are side view illustrations of the deflecting segment of FIG. 6A, wherein the deflecting segment is formed to have a deflected state at various angles of deflection in accordance with further embodiments hereof, and wherein the heart valve prosthesis has been omitted for clarity.
Figure 14D:
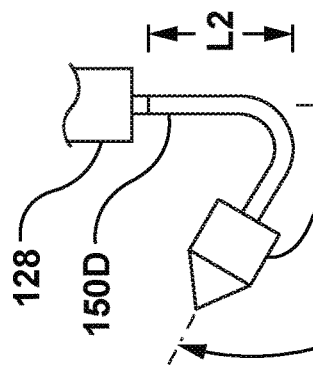
Figure 14C:
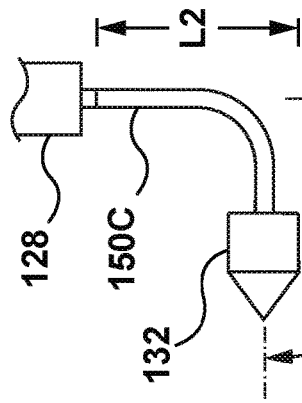
Figure 14B:
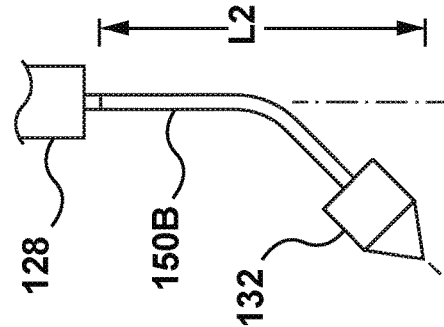
Figure 14A:
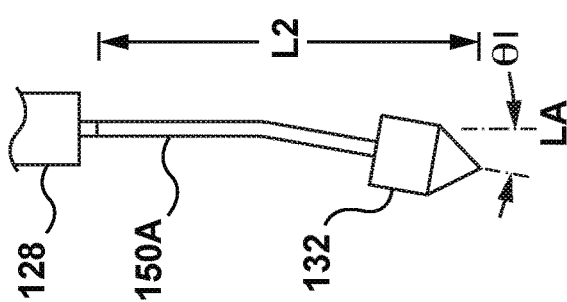

With reference to FIG. 13, with the distal end 142 of the outer sheath 128 positioned at the outflow portion 108 of the heart valve prosthesis 100, the second actuation mechanism 138 (not shown in FIGS. 8-13) of the handle 126 (not shown in FIGS. 8-13) is manipulated to proximally retract the inner shaft assembly 130 (not shown in FIG. 13). As the deflecting segment 150 (obscured from view in FIG. 13 by the outer sheath 128 and the distal nosecone 132) is received within and constrained by the outer sheath 128, the deflecting segment 150 is forced to straighten or realign with the central longitudinal axis LA of the distal portion 155 (obscured from view in FIG. 13 by the outer sheath 128 and distal nosecone 132) of the inner shaft 154, thereby transitioning from the deflected state to the delivery state for removal.

While the method of FIGS. 8-13 is described with the deflecting segment 150 of FIGS. 5A-5B, it will be apparent that other embodiments of the deflecting segment may be utilized the method, including, but not limited to the deflecting segment 150' of FIGS. 6A-6B.

Although the method of FIGS. 8-13 utilizes the heart valve prosthesis 100 of FIG. 3A, the method may be adapted for use with various other heart valve prostheses, as described above. Further, the method may be used at other locations within the patient.

While the deflecting segment 150 has been described as deflecting to a substantially U-shape, or at an angle of deflection θ1 of substantially 180° from the central longitudinal axis LA of the distal portion 155 of the inner shaft 154, as shown in FIG. 6B, this is not meant to be limiting. As shown in FIGS. 14A-14E, a deflecting segment 150A, 150B, 150C, 150D, 150E may be shape-set to laterally deflect in relation to the central longitudinal axis LA of an inner shaft 154 to other angles of deflection θ1 such that a first axial or longitudinal length L1 (FIG. 6A) with the respective deflecting segment in a delivery state is greater than a second axial or longitudinal length L2 with the respective deflecting segment in a deflected state. For example, and not by way of limitation, the deflecting segments 150A, 150B, 150C, 150D, 150E may be shape-set to deflect to an angle of deflection θ1 of substantially 10° (FIG. 14A), 20°, 30°, 45° (FIG. 14B), 90° (FIG. 14C), 120° (FIG. 14D), 135° (FIG. 14E), or any other angle of deflection from substantially 0° to 180°. Somewhat similar to a second axial length L2' of the embodiment of FIG. 7B, in the embodiments of FIGS. 14A, 14B and 14C, a second axial or longitudinal length L2 of the respective deflecting segment 150A, 150B, 150C in a deflected state includes a length of the respective deflecting segment 150A, 150B, 150C in a deflected state in combination with at least a portion of a length and/or width of the laterally displaced nosecone 132 that is distal of the distal end of the respective deflecting segment.

While various embodiments according to the present invention have been described above, it should be understood that they have been presented by way of illustration and example only, and not limitation. Various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of delivering, positioning and deploying a heart valve prosthesis at a site of a native heart valve, the method comprising the steps of:

advancing a delivery catheter with a heart valve prosthesis in a radially collapsed configuration retained therein to a native heart valve of a heart, wherein the delivery catheter includes an outer sheath and an inner shaft assembly, the inner shaft assembly including an inner shaft, a deflecting segment in a delivery state, and a distal nosecone;

positioning the delivery catheter with the heart valve prosthesis in the radially collapsed configuration at a native heart valve;

retracting the outer sheath of the delivery catheter to release a first portion of the heart valve prosthesis;

advancing the delivery catheter such that the first portion of the heart valve prosthesis engages tissue of the native heart valve;

advancing the inner shaft assembly such that the distal nosecone releases a second portion of the heart valve prosthesis and the deflecting segment transitions from the delivery state to a deflected state by axially collapsing a portion of the deflecting segment, along with the distal nosecone, proximally along the central longitudinal axis of the distal portion of the inner shaft;

advancing the outer sheath of the delivery catheter such that the outer sheath advances through the heart valve prosthesis; and retracting the inner shaft assembly such that the deflecting segment transitions from the deflected state to the delivery state as it is received within a distal portion of the outer sheath.

2. The method of claim 1, wherein the native heart valve is a native mitral valve.

3. The method of claim 2, wherein the first portion of the heart valve prosthesis is an inflow portion and the second portion of the heart valve prosthesis is an outflow portion, and wherein the step of advancing the delivery catheter such that the first portion of the heart valve prosthesis engages tissue of the native heart valve permits the inflow portion of the heart valve prosthesis to return to an expanded state within an atrial area of the native mitral valve, and wherein the step of advancing the inner shaft assembly such that the distal nosecone releases the second portion of the heart valve prosthesis permits the outflow portion of the heart valve prosthesis to return to an expanded state within an annulus of the native mitral valve.

4. The method of claim 2, wherein the step of positioning the delivery catheter with the heart valve prosthesis in the radially collapsed configuration at a native heart valve includes a transseptal delivery approach to the native mitral valve.

5. The method of claim 1, wherein the deflecting segment is shape-set to a deflected state and the heart valve prosthesis and/or the distal nosecone maintains the deflecting segment in the delivery state during advancing of the delivery catheter.

6. The method of claim 5, wherein the deflecting segment transitions from the delivery state to the deflected state due to being shape-set to the deflected state.

7. The method of claim 1, wherein the portion of the deflecting segment deflects into a wavy form in the deflected state.

8. The method of claim 1, the portion of the deflecting segment deflects into a coiled form in the deflected state.

9. A delivery system comprising:
a delivery catheter comprising:
an outer sheath;
an inner shaft slidably disposed within the outer sheath;
a distal nosecone at a distal portion of the delivery catheter; and
a deflecting segment including a proximal end coupled to the inner shaft and a distal end coupled to the distal nosecone, wherein the deflecting segment has a delivery state and a deflected state, wherein when the deflecting segment is in the delivery state, the deflecting segment and the distal nosecone have a combined first longitudinal length along a central longitudinal axis of a distal portion of the inner shaft, and when the deflecting segment is in the deflected state, the deflecting segment has a second longitudinal length along the central longitudinal axis, wherein the combined first longitudinal length is greater than the second longitudinal length, and wherein the deflecting segment transitions from the delivery state to the deflected state by axially collapsing a portion of the deflecting segment, along with the distal nosecone, proximally along the central longitudinal axis of the distal portion of the inner shaft.

10. The delivery system of claim 9, wherein when the deflecting segment is in the deflected state, the deflecting segment has a wavy form.

11. The delivery system of claim 9, wherein when the deflecting segment is in the deflected state, the deflecting segment has a coiled form.

12. The delivery system of claim 9, further comprising a heart valve prosthesis having a radially collapsed configuration and a radially expanded configuration.

13. The delivery system of claim 12, wherein the heart valve prosthesis is a mitral heart valve prosthesis.

14. The delivery system of claim 9, wherein the deflecting segment is shape-set to the deflected state and is held in the delivery state by the heart valve prosthesis or by the outer sheath.

* * * * *